United States Patent
Nakagawa et al.

(10) Patent No.: US 10,613,206 B2
(45) Date of Patent: Apr. 7, 2020

(54) ULTRASOUND PROBE AND ULTRASOUND IMAGING APPARATUS USING THE SAME

(71) Applicant: HITACHI, LTD., Tokyo (JP)

(72) Inventors: Tatsuo Nakagawa, Tokyo (JP); Hiroshi Masuzawa, Tokyo (JP); Shinya Kajiyama, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 616 days.

(21) Appl. No.: 15/121,418

(22) PCT Filed: Feb. 26, 2014

(86) PCT No.: PCT/JP2014/054756
§ 371 (c)(1),
(2) Date: Aug. 25, 2016

(87) PCT Pub. No.: WO2015/128974
PCT Pub. Date: Sep. 3, 2015

(65) Prior Publication Data
US 2016/0363657 A1 Dec. 15, 2016

(51) Int. Cl.
*G01S 7/52* (2006.01)
*G01S 15/89* (2006.01)
(Continued)

(52) U.S. Cl.
CPC .......... *G01S 7/52046* (2013.01); *A61B 8/145* (2013.01); *A61B 8/4444* (2013.01);
(Continued)

(58) Field of Classification Search
CPC ............. G01S 7/52046; G01S 7/52025; G01S 7/5208; G01S 15/8915; G10K 11/346;
(Continued)

(56) References Cited

U.S. PATENT DOCUMENTS 5,388,079 A  2/1995 Kim et al.
6,500,120 B1 * 12/2002 Anthony ............... G01S 7/5208
                                                       600/437
(Continued)

FOREIGN PATENT DOCUMENTS

CN  102680978 A  9/2012
CN  103076603 A  5/2013
(Continued)

OTHER PUBLICATIONS

Chinese Office Action received in corresponding Chinese Application No. 201480076530.2 dated Jul. 11, 2018.
(Continued)

*Primary Examiner* — Theodore J Stigell
*Assistant Examiner* — Sean A Frith
(74) *Attorney, Agent, or Firm* — Mattingly & Malur, PC

(57) ABSTRACT

A compact delay circuit that can dynamically change delay time is configured. A probe includes an analog memory unit that accumulates electric charges corresponding to a reflected wave of an ultrasonic wave produced by a difference between the acoustic impedances on a plurality of capacitors 303 and in turn outputs the electric charges accumulated on the capacitors 303 to an analog memory unit 205. In accumulating electric charges, when a control signal Ctls_1 that increases delay time of the reflected wave is inputted, the analog memory unit 205 accumulates the same electric charges on two or more of the capacitors 303 for a preset period, or in outputting electric charges, when a control signal Ctlo_1 is inputted, the analog memory unit 205 outputs the electric charges accumulated on one of the capacitors 303 for a preset period.

7 Claims, 18 Drawing Sheets

(51) Int. Cl.
*G10K 11/34* (2006.01)
*A61B 8/08* (2006.01)
*A61K 8/14* (2006.01)
*A61K 8/00* (2006.01)
*A61B 8/14* (2006.01)
*A61B 8/00* (2006.01)

(52) U.S. Cl.
CPC .......... *A61B 8/4494* (2013.01); *A61B 8/5207* (2013.01); *G01S 7/5208* (2013.01); *G01S 7/52025* (2013.01); *G01S 15/8915* (2013.01); *G10K 11/346* (2013.01)

(58) Field of Classification Search
CPC ..... A61B 8/145; A61B 8/4444; A61B 8/4494; A61B 8/5207
See application file for complete search history.

(56) References Cited

U.S. PATENT DOCUMENTS

| | | | |
|---|---|---|---|
| 8,177,718 B2 | 5/2012 | Savord | |
| 9,091,749 B2 | 7/2015 | Amemiya | |
| 2007/0225604 A1* | 9/2007 | Fukukita | G01S 15/8925 600/437 |
| 2012/0197130 A1 | 8/2012 | Amemiya et al. | |
| 2012/0310096 A1 | 12/2012 | Hongou et al. | |
| 2013/0107671 A1* | 5/2013 | Amemiya | G01S 7/52026 367/135 |

FOREIGN PATENT DOCUMENTS

| | | | |
|---|---|---|---|
| EP | 2 482 095 A2 | 8/2012 | |
| EP | 2482095 A2 * | 8/2012 | ......... G01S 7/52025 |
| JP | 08-505556 A | 6/1996 | |
| JP | 10-127629 A | 5/1998 | |
| JP | 2009-528115 A | 8/2009 | |
| JP | 2012-152432 A | 8/2012 | |
| JP | 2013-106931 A | 6/2013 | |
| WO | 2006/035588 A1 | 4/2006 | |

OTHER PUBLICATIONS

Japanese Office Action received in corresponding Japanese Application No. 2016-504919 dated Jun. 13, 2017 with partial translation.
"The Revised Handbook of Medical Equipment", Electronic Industries Association of Japan, Jan. 20, 1997, p. 108, Corona Publishing, Japan with partial translation.
Communication Pursuant to Rule 164(1) EPC received in corresponding European Application No. 14883577.0 dated Oct. 9, 2017.
Extended European Search Report received in corresponding European Application No. 14883577.0 dated Feb. 5, 2018.

* cited by examiner

ULTRASOUND PROBE AND ULTRASOUND IMAGING APPARATUS USING THE SAME

TECHNICAL FIELD

The present invention relates to an ultrasound probe and an ultrasound imaging apparatus using the same, and more specifically to a technique effective for dynamically delaying ultrasound signals inputted to an ultrasound probe.

BACKGROUND ART

Compared with medical imaging diagnostic devices, such as an X-ray diagnostic device and an MRI (Magnetic Resonance Imaging) device, an ultrasound imaging apparatus is a compact device that can display the motion of an object to be tested, such as the pulsatory motion of a heart and the motion of a fetus, in real time with simple operations by putting an ultrasound probe on the body surface.

Specifically, in the ultrasound imaging apparatus, drive signals are supplied to each of a plurality of transducers built in the ultrasound probe, and ultrasonic waves are transmitted to the inside of an examinee. In the ultrasound imaging apparatus, the reflected waves of the ultrasonic waves produced by the difference between the acoustic impedances of biological tissues are received by the plurality of transducers, and an ultrasound image is generated based on the reflected waves received by the ultrasound probe.

Here, in order to improve the image quality of ultrasound images, the ultrasound imaging apparatus controls delay time over drive signals supplied to the plurality of transducers and over reflected wave signals obtained from each of the plurality of transducers.

Specifically, in the ultrasound imaging apparatus, the timing of drive signals supplied to the transducers is controlled based on delay time corresponding to the distance between a predetermined focal point in the inside of the examinee and each of the transducers, and a beam of ultrasonic waves is transmitted to the predetermined focal point in the inside of the examinee.

Based on the delay time corresponding to the distance between the predetermined focal point in the inside of the examinee and each of the transducers, the transducers receive signals from the predetermined focal point differently in terms of time, and the signals are added as their time is matched, i.e. the signals are phased and added. Thus, the ultrasound imaging apparatus generates a line of received signals in focus. As described above, an analog or digital delay circuit is necessary in order to match the signals from a predetermined focal point.

For example, Patent Literature 1 discloses a configuration, in which an echo signal current is accumulated on capacitor banks at a predetermined timing for providing delay time. Patent Literature 2 describes a technique, in which current signals are generated with suitable delay time based on a write pointer and a read pointer from sampled echo signals.

CITATION LIST

Patent Literature

Patent Literature 1: Japanese Unexamined Patent Application Publication No. 2013-106931
Patent Literature 2: Japanese Unexamined Patent Application Publication (Translation of PCT Application) No. 2009-528115

SUMMARY OF INVENTION

Technical Problem

In order to obtain a three-dimensional stereo image, not a two-dimensional tomographic image, a two-dimensional probe, which has transducers in a two-dimensional array, uses transducers in a few thousands to ten thousands channels.

In such a two-dimensional probe, connecting all the transducers to a main device is impractical because of the restriction on the number of cables, for example. A process is required, in which the number of channels is decreased in the inside of a probe head. Thus, an electronic circuit that delays and adds analog signals is needed.

Also in a linear probe, delaying and adding analog signals can decrease the number of cables and the number of analog to digital converters, allowing a reduction in cost and downsizing. To this end, an electronic circuit that delays and adds analog signals is demanded.

In the case where a circuit that delays analog signals is mounted in the inside of the probe head, it is necessary to configure the circuit in a small size. This is because circuits, which are connected to transducers in a few thousands to ten thousands channels, have to be mounted in the inside of a probe head. In order to highly accurately achieve the focal point of a reception beam by the transducers, it is required to change delay time given by each of the circuits in terms of time.

For a configuration of changing delay time, a configuration is designed, for example, in which a plurality of delay circuits are provided, the delay circuits are operated at different periods of delay time, and a delay circuit to be used is switched at certain timing.

In this configuration, while a circuit is operating, another delay time can be set to another circuit. In dynamically changing delay time, circuits connected to the output are switched for use. Thus, delay time can be changed.

However, in such a circuit, a plurality of similar delay circuits are required, resulting in the necessity of circuits that need a large area. This upsizes the ultrasound probe, causing a problem of a cost increase.

An object of the present invention is to provide a technique that can dynamically change delay time and can configure a compact delay circuit.

The foregoing object, other objects, and novel features of the present invention will be apparent from the description of the present specification and the accompanying drawings.

Solution to Problem

In the present application, a brief outline of representative aspects of the disclosure is as follows.

A representative ultrasound probe includes a delay unit. The delay unit accumulates electric charges corresponding to a reflected wave of an ultrasonic wave produced by a difference between acoustic impedances on a plurality of memory elements and in turn outputs the electric charges accumulated on the memory elements.

In accumulating the electric charges, when a first control signal that increases delay time of the reflected wave is inputted, the delay unit accumulates the same electric charges on two or more of the memory elements for a preset period. Alternatively, in outputting the electric charges, when the first control signal is inputted, the delay unit outputs electric charges accumulated on one of the memory elements for a preset period.

In accumulating the electric charges, when a second control signal that decreases delay time of the reflected wave is inputted, the delay unit of the representative ultrasound probe accumulates the same electric charges on one of the memory elements for a preset period. Alternatively, in outputting the electric charges, when the second control signal is inputted, the delay unit outputs no electric charges from the memory elements for a preset period.

The delay unit is also applied to an ultrasound imaging apparatus using the ultrasound probe.

Advantageous Effects of Invention (1) It is possible to downsize the delay circuit that dynamically changes the delay time of ultrasound signals in the ultrasound probe.

(2) From the effect (1), the ultrasound probe can be downsized.

(3) From the effect (1), the costs of the ultrasound probe can be decreased.

DESCRIPTION OF EMBODIMENTS

Figure 1:
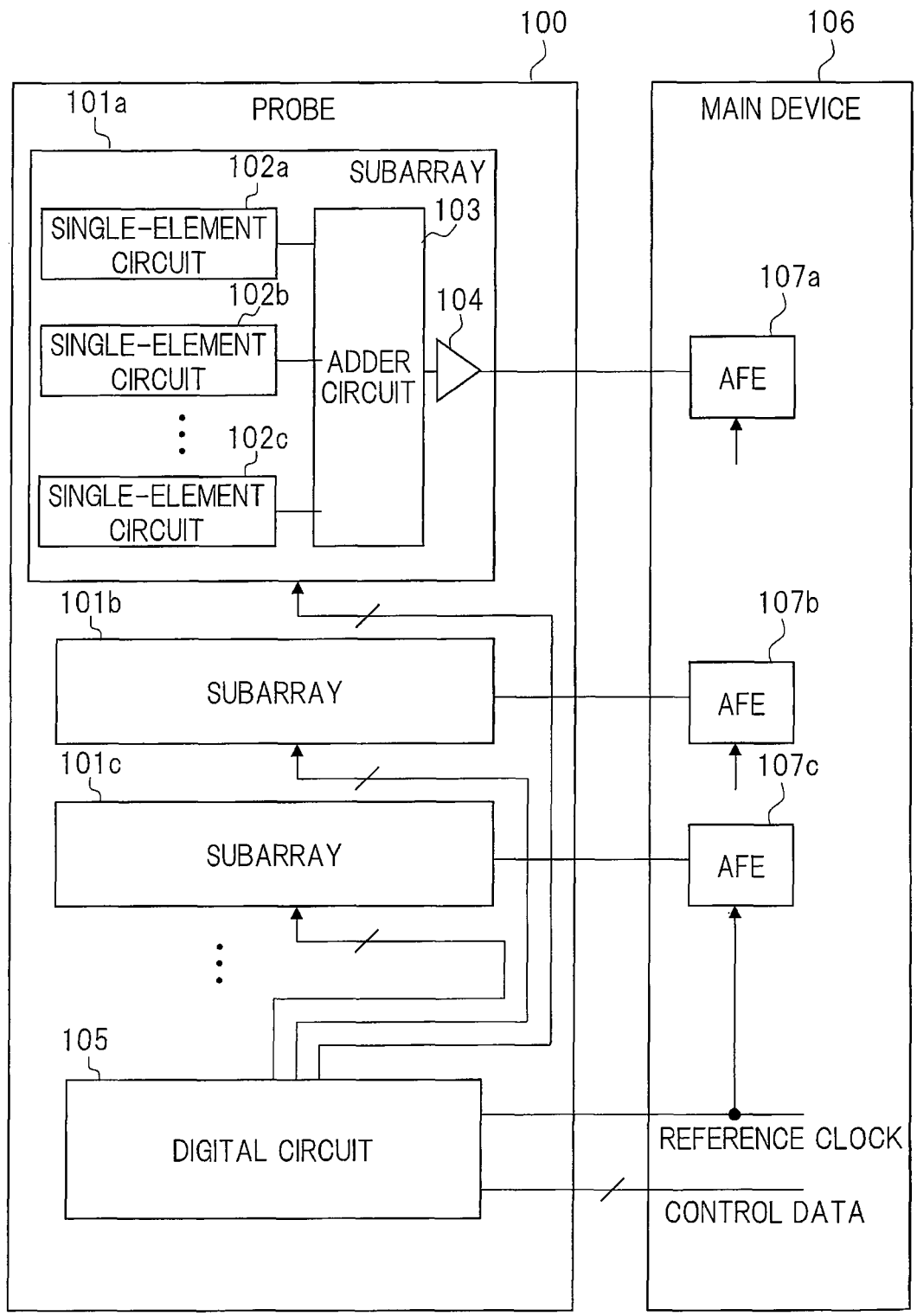
FIG. 1 is a block diagram of an exemplary ultrasound imaging apparatus according to a first embodiment.

In the embodiments below, the present invention will be described as separated into a plurality of sections or embodiments, as necessary for convenience. The sections or the embodiments have some relationship to each other unless otherwise specified. In the relationship, one is an exemplary modification, details, or supplementary explanation, for example, of a part or entirety of the other.

In the embodiments below, in terms of the figures of elements, including the numbers of elements, numeric values, quantities, and ranges, any figures can be used, which may be specific numbers or more or specific numbers or less, unless otherwise specified, or theoretically clearly limited to a specific figure.

In the embodiments below, it goes without saying that the components of the embodiments (including element steps and the like) are not necessarily required, unless otherwise specified and theoretically clearly required.

Similarly, in the embodiments below, in terms of the shapes of the components and the positional relationship between the components, for example, ones substantially analog or similar to the shapes and the positional relationship are included, unless otherwise specified, or theoretically clearly different. The same is applied to the numeric values and the ranges above.

In all the drawings for explaining the embodiments, the same members are designated the same reference numerals and signs in principle, and the overlapping description is omitted. Note that, for easy understanding of the drawings, even plan views are sometimes hatched.

In the following, the embodiments will be described in detail.

First Embodiment

FIG. 1 is a block diagram of an exemplary ultrasound imaging apparatus according to a first embodiment.

As illustrated in FIG. 1, the ultrasound imaging apparatus includes a probe 100 and a main device 106. The probe 100 includes a plurality of subarrays 101a, 101b, . . . , and a digital circuit 105 that is a control signal generating unit.

The subarray 101 includes a plurality of single-element circuits 102a, 102b, . . . , an adder circuit 103, and a buffer 104. 128 subarrays 101 are provided, for example. The single-element circuits 102 are arrayed in a matrix configuration by approximately 8×8=64.

The main device 106 includes a plurality of analog front end circuits (written by AFE in FIG. 1) 107a, 107b, .... One analog front end circuit 107 is provided for one subarray 101. Note that, in the following, subscripts a, b, c, ... express the same components, and are omitted unless otherwise specified.

Figure 2:
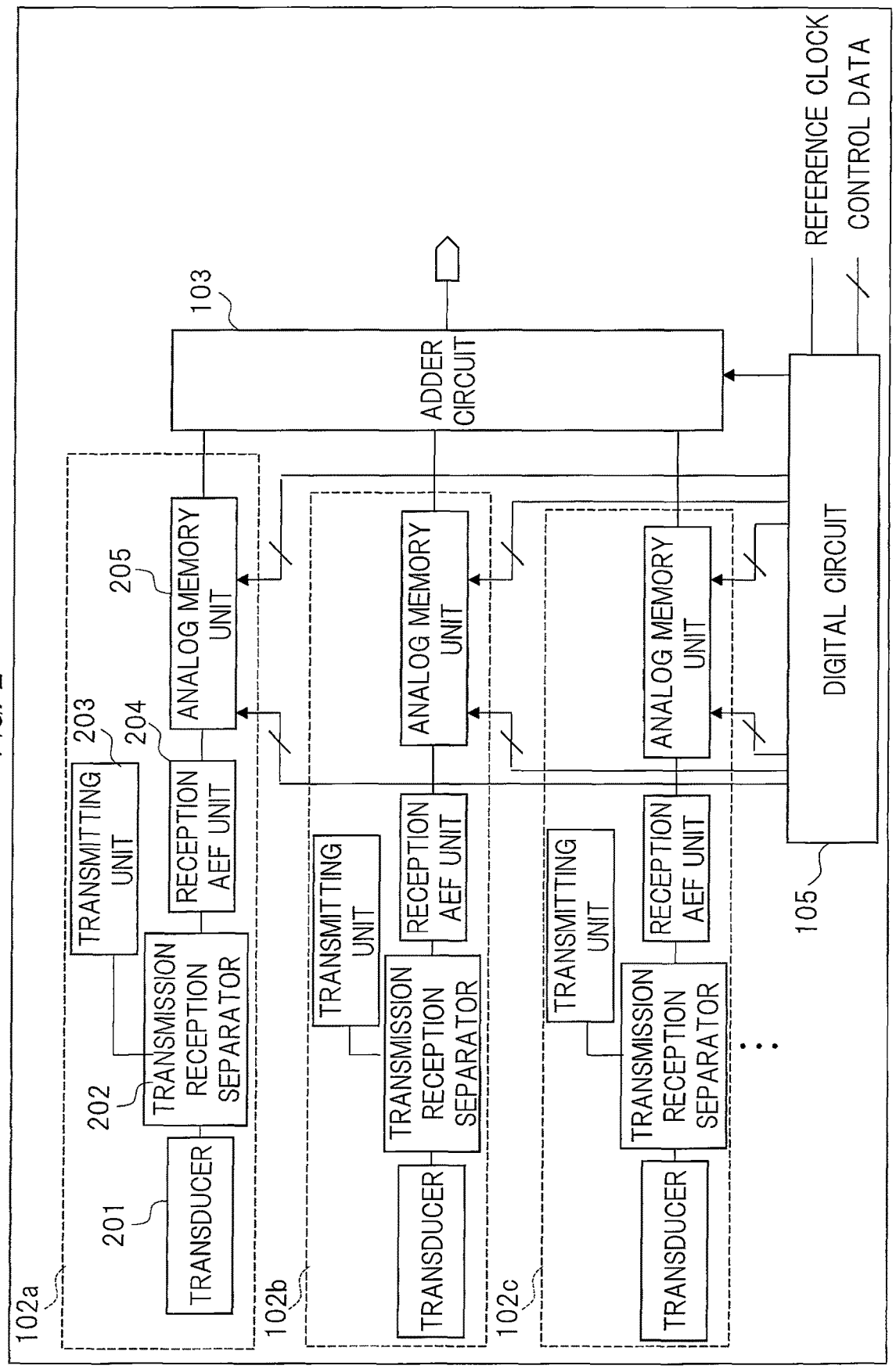
FIG. 2 is a block diagram of an exemplary configuration of a single-element circuit of a probe in FIG. 1.

FIG. 2 is a block diagram of an exemplary configuration of the single-element circuit 102 of the probe 100 in FIG. 1.

As illustrated in the drawing, the single-element circuit 102, which is a transmitter-receiver unit, is configured of a transducer 201, a transmitting unit 203, a transmission reception separator 202, a reception analog front end unit (in FIG. 2, written by the reception AFE UNIT) 204, and an analog memory unit 205, which is a voltage storage output unit. The digital circuit 105 and the analog memory unit 205 configure a delay unit.

Signals outputted from the transmitting unit 203 are separated at the transmission reception separator 202, and sent to the transducer 201. The transducer 201 outputs ultrasound signals. The ultrasound signals outputted from the transducer 201 are reflected, and then received at the transducer 201.

The ultrasound signals received at the transducer 201 are separated at the transmission reception separator 202, and inputted to the reception analog front end unit 204. The reception analog front end unit 204 processes, e.g. amplifies and filters, the received signals.

The signals outputted from the reception analog front end unit 204 are inputted to the analog memory unit 205. Based on control signals outputted from the digital circuit 105, the analog memory unit 205 samples analog input signals and accumulates the signals on its memory, and outputs the signals after a lapse of delay time.

The control signal that sets delay time is set at the digital circuit 105 based on a reference clock and control data from the main device 106. The signals outputted from the analog memory unit 205 are outputted from the single-element circuit 102 to the adder circuit 103, and added at the adder circuit 103.

The signals added at the adder circuit 103 are sent to the analog front end circuit 107 of the main device 106 through the buffer 104 in FIG. 1.

Figure 3:
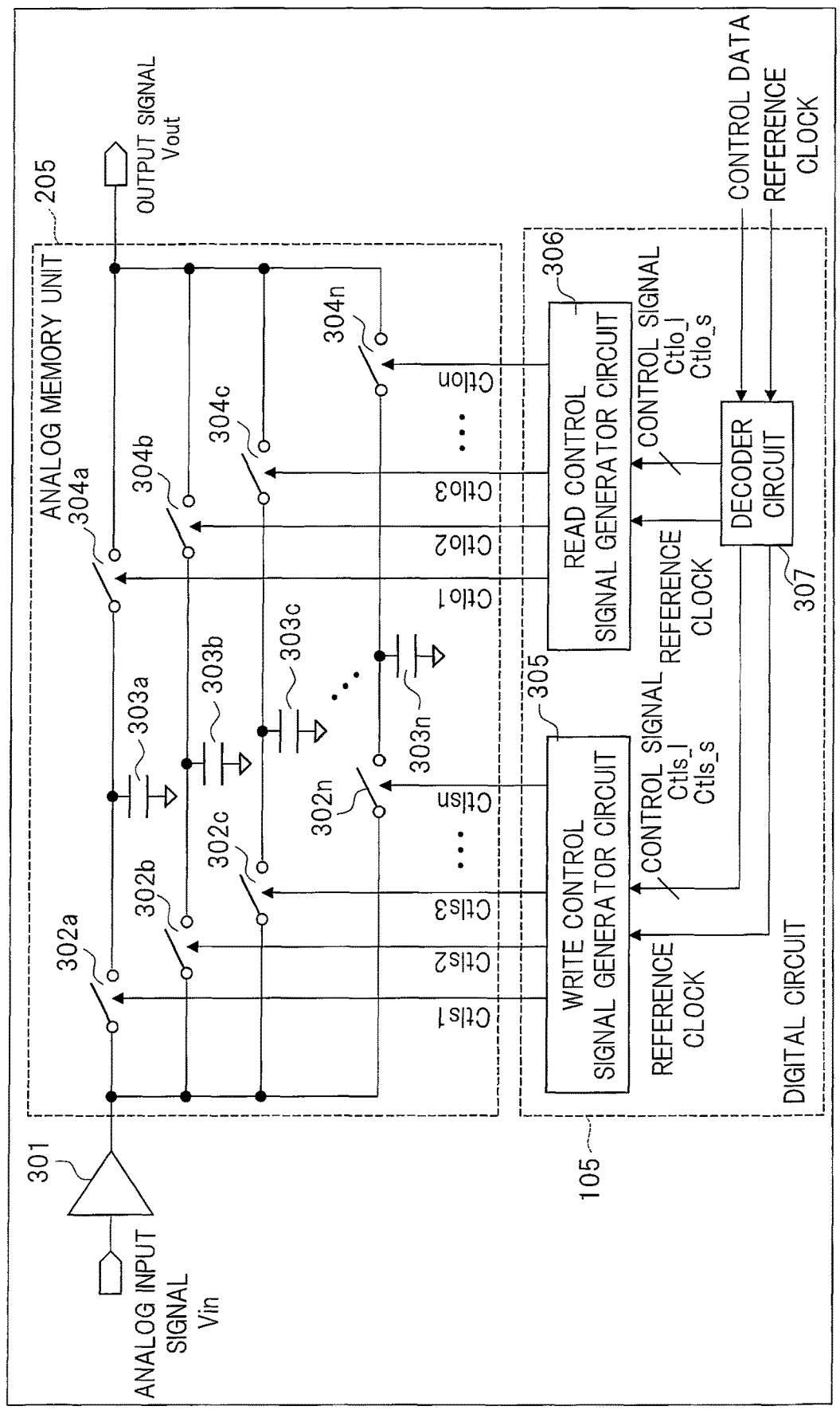
FIG. 3 is a block diagram of an exemplary analog memory unit and an exemplary digital circuit of the single-element circuit in FIG. 2.

FIG. 3 is a block diagram of examples of the analog memory unit 205 of the single-element circuit 102 in FIG. 2 and the digital circuit 105.

As illustrated in the drawing, the analog memory unit 205 includes capacitors 303a, 303b, 303c, ..., which are memory elements, switches 302a, 302b, 302c, ..., which are first switches, switches 304a, 304b, 304c, ..., which are second switches, and a buffer 301. The digital circuit 105 includes a write control signal generator circuit 305, a read control signal generator circuit 306, and a decoder circuit 307.

To the output part of the buffer 301, one end of the switch 302 is in common connection. To the other end of the switch 302, one end of the switch 304 and one connecting part of the capacitor 303 are connected.

To the other connecting part of the capacitor 303, a reference potential VSS is connected. The other end of the switch 304 is in common connection. The common connecting part is the output part of the analog memory unit 205.

The control terminal of the switch 302 is connected to the write control signal generator circuit 305 in such a manner that write control signals Ctls1 to Ctlsn outputted from the circuit 305 are inputted respectively. The write control signal generator circuit 305 generates the write control signals Ctls1 to Ctlsn based on the reference clock outputted from the main device 106.

The control terminal of the switch 304 is connected to the read control signal generator circuit 306 in such a manner that read control signals Ctlo1 to Ctlon outputted from the circuit 306 are inputted respectively. The read control signal generator circuit 306 generates the read control signals Ctlo1 to Ctlon based on the reference clock outputted from the main device 106.

An analog input signal Vin outputted from the reception analog front end unit 204 is amplified or its impedance is converted at the buffer 301, and then inputted to the capacitor 303 through the switch 302. Thus, electric charges corresponding to the analog input signal Vin are accumulated.

The electric charges accumulated on the capacitor 303 are outputted as an output signal Vout from the output part of the analog memory unit 205 through the switch 304.

The analog memory unit 205 is a delay generator circuit. In the analog memory unit 205, the capacitors 303 are connected in parallel with each other, the analog input signal Vin is sampled and in turn stored, and the stored signals are in turn outputted after a lapse of a predetermined period of time. Note that, the buffer 301 may also serve as the circuit of the reception analog front end unit 204 in the previous stage.

The timing of charging signals on the capacitor 303 is controlled by the switch 302, and the timing of outputting signals from the capacitor 303 is controlled by the switch 304. The write control signals Ctls1 to Ctlsn that control the operation of the switch 302 are generated by the write control signal generator circuit 305 of the digital circuit 105. The read control signals Ctlo1 to Ctlon that control the operation of the switch 304 are generated by the read control signal generator circuit 306 of the digital circuit 105.

The decoder circuit 307 decodes control data outputted from the main device 106, and outputs the decoded result as control signals to the write control signal generator circuit 305 and the read control signal generator circuit 306.

The control signals outputted from the decoder circuit 307 include control signal Ctls_l, control signal Ctls_s, control signal Ctlo_l, and control signal Ctlo_s. The control signal Ctls_l, control signal Ctls_s, control signal Ctlo_l, and control signal Ctlo_s are delay time control signals. The control signals Ctls_l and Ctlo_l are first control signals. The control signals Ctls_s and Ctlo_s are second control signals.

The control signals Ctls_l and Ctls_s are outputted to the write control signal generator circuit 305. The control signals Ctlo_l and Ctlo_s are outputted to the read control signal generator circuit 306.

The control signal Ctls_l is a signal that increases write-side delay time at the analog memory unit 205. The control signal Ctls_s is a signal that decreases write-side delay time at the analog memory unit 205.

The control signal Ctlo_l is a signal that increases read-side delay time at the analog memory unit 205. The control signal Ctlo_s is a signal that decreases read-side delay time at the analog memory unit 205.

The write control signal generator circuit 305 and the read control signal generator circuit 306 generate the write control signals Ctls1 to Ctlsn and the read control signals Ctlo1 to Ctlon based on the control signals outputted from the decoder circuit 307.

Figure 4:
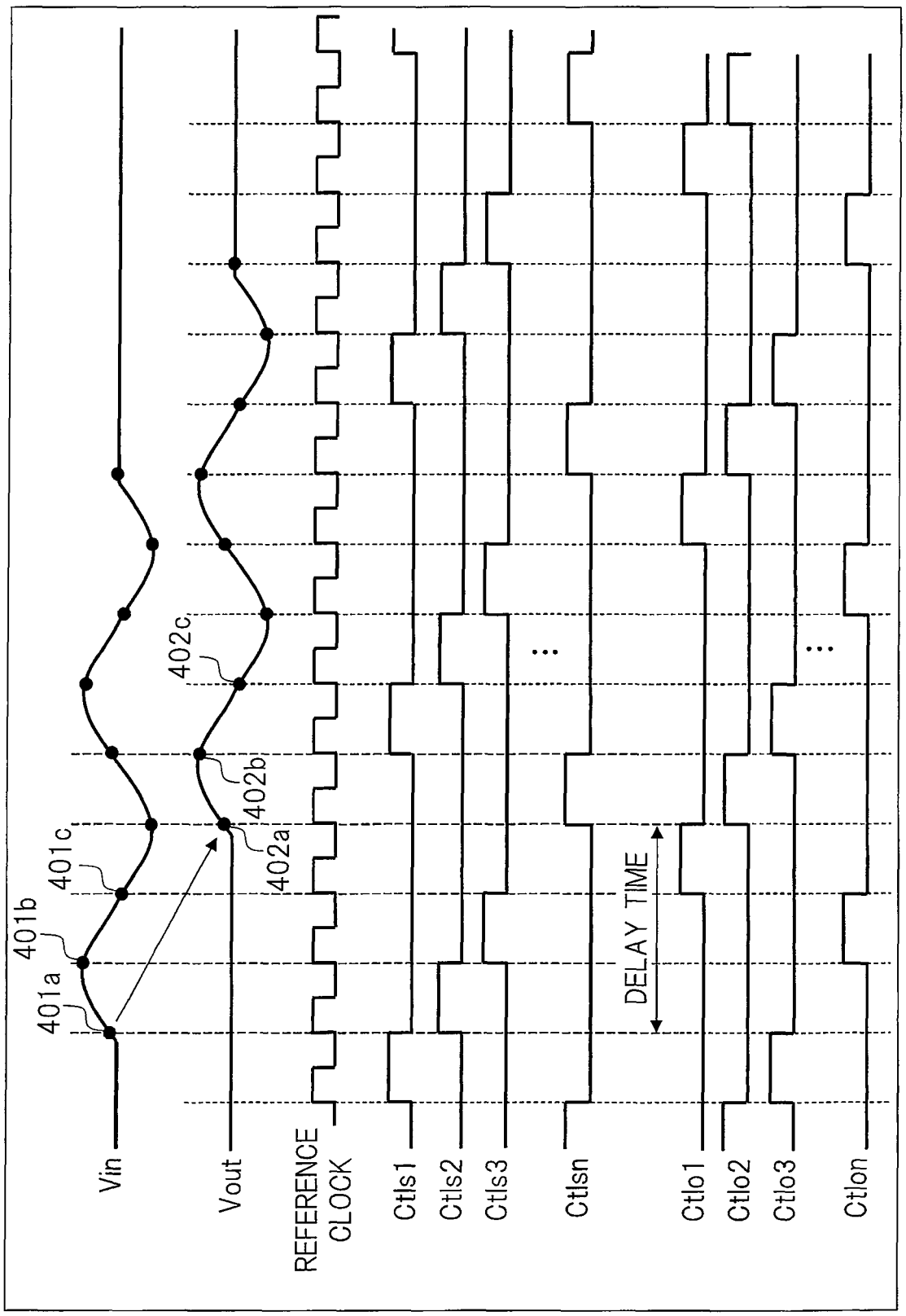
FIG. 4 is a timing chart of an example of the operation of the analog memory unit in FIG. 3.

FIG. 4 is a timing chart of an example of the operation of the analog memory unit 205 in FIG. 3.

From the upper side to the lower side, FIG. 4 shows signal timings for the analog input signal Vin inputted to the analog memory unit 205, the output signal Vout outputted from the analog memory unit 205, the reference clock inputted to the write control signal generator circuit 305 and the read control signal generator circuit 306, the write control signals Ctls1 to Ctlsn, and the read control signals Ctlo1 to Ctlon.

As illustrated in FIG. 3, the write control signal Ctls1 controls the switch 302a. Here, in FIG. 3, the switch 302a is turned on in the case where the write control signal Ctls1 is at high level, although any polarity is possible.

When the switch 302a is turned on, electric charges corresponding to the analog input signal Vin are accumulated on the capacitor 303a. The value of the analog input signal at the timing, at which the switch 302a is changed from on to off, is stored on the capacitor 303a (401a in FIG. 4).

The electric charges accumulated on the capacitor 303a are outputted to the output signal Vout in the state in which the switch 304a is turned on (402a in FIG. 4). The control signal Ctlo1 controls the timing of turning on/off the switch 304a. In other words, the signal sampled on the capacitor 303a at the timing of the write control signal Ctls1 is outputted as the output signal Vout at the timing at which the control signal Ctlo1 is turned on.

Similarly to the capacitor 303a, electric charges corresponding to the analog input signal Vin are accumulated on the capacitors 303b, 303c, . . . , which are arrayed in parallel with each other, at the timings of the write control signals Ctls2 and Ctls3, . . . , and signals corresponding to the electric charges accumulated at the timings of turning on the control signal Ctlo2, Ctlo3, . . . are outputted as the output signal Vout.

As described above, the signals sampled at the timing of the write control signal Ctls are outputted at the timing of the control signal Ctlo. Thus, compared with the analog input signal Vin, the output signal Vout is outputted, which is delayed with the delay time of the write control signal Ctls and the delay time of the read control signal Ctlo.

As described above, the write control signal Ctls and the read control signal Ctlo are generated at the write control signal generator circuit 305 and the read control signal generator circuit 306, respectively. For delay time, for example, a clock cycle Tclk for the reference clock is defined as a unit, and an integral multiple of the clock cycle Tclk is set as delay time. In other words, delay time Tdc=M·Tclk, based on the clock, is generated, where M is an integer.

In receiving ultrasound signals, in order to highly accurately receive ultrasound signals, which have been reflected in the inside of a living body and returned, it is necessary to receive the ultrasound signals as the position of the focal point is moved in terms of time. In order to dynamically change the focal point in the circuits in the inside of the probe 100, it is necessary to dynamically change delay time while receiving ultrasound signals. Specifically, it is necessary to increase or decrease delay time by comparing the delay time with set time.

Referring to FIGS. 5 to 8, the operation in dynamically changing delay time will be described.

Figure 5:
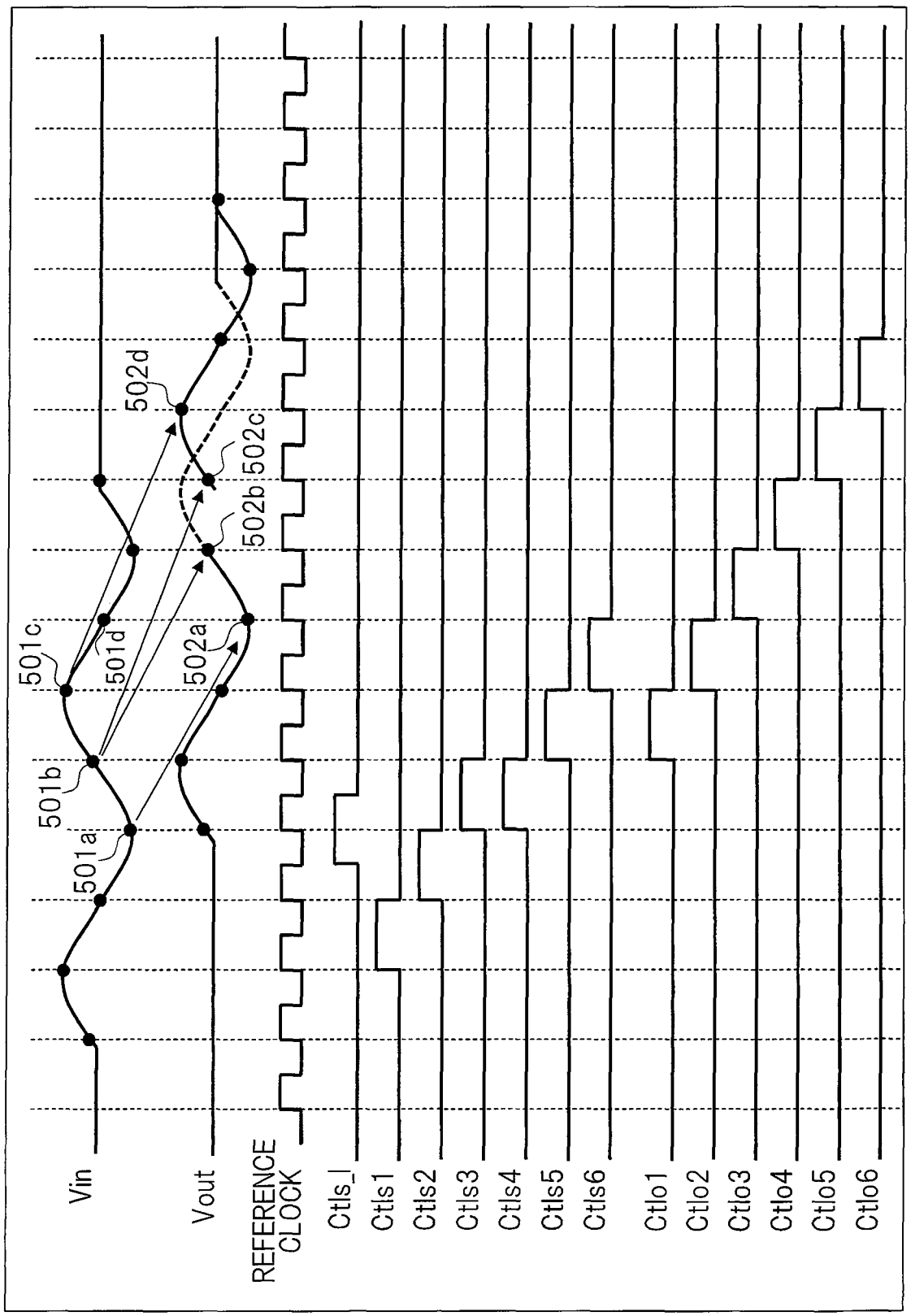
FIG. 5 is a timing chart of an example in dynamically changing delay time in the analog memory unit in FIG. 3.

FIG. 5 is a timing chart of an example in dynamically changing delay time in the analog memory unit 205 in FIG. 3.

From the upper side to the lower side, FIG. 5 shows signal timings for the analog input signal Vin inputted to the analog memory unit 205, the output signal Vout outputted from the analog memory unit 205, the reference clock, the control signal Ctls_l outputted from the decoder circuit 307, the write control signals Ctls1 to Ctls6, and the read control signals Ctlo1 to Ctlo6.

First, a signal 501a sampled at the timing of the write control signal Ctls2 in FIG. 5 is outputted at the timing of the control signal Ctlo2 after a lapse of a predetermined period of delay time (502a in FIG. 5).

Here, in the case where the write control signals Ctls are controlled to increase delay time, the same input signal Vin is written to the capacitors 303. In the case where the control signal Ctls_l that increases delay time is outputted from the decoder circuit 307, the write control signals Ctls are turned to high level at the same time, and the switches 302 are turned on at the same time.

In this case, an example is shown in which the control signal Ctls_l is outputted for turning the control signals Ctls3 and Ctls4 to high level at the same time. Thus, the input signal Vin (501b in FIG. 5) is sampled on two capacitors 303c and 303d.

Data stored on the capacitor 303c is outputted at the timing at which the read control signal Ctlo3 is turned on (502b in FIG. 5).

Data stored on the capacitor 303d is outputted at the timing at which the read control signal Ctlo4 is turned on (502c in FIG. 5). The signals accumulated on the capacitors 303c and 303d are signals at the same timing (501b in FIG. 5). Thus, the same signals are outputted at different timings.

A signal 501c in FIG. 5 sampled at the timing of the write control signal Ctls5 is outputted at the timing of the read control signal Ctlo5 (502d in FIG. 5). Compared with the state before the control signal Ctls_l that increases delay time is outputted, the signal at the same timing is outputted for two samples. Thus, delay time can be increased.

In the case where the write control signal is controlled, the signals are controlled to be written to the capacitors so as not to read capacitors with no written data, even in the case of changing delay time. Signals are outputted also when delay time is changed. Thus, the influence of noise is small in switching delay time.

Note that, in the first embodiment, the description is made in which signals are sampled on two capacitors at the same time. However, the number of capacitors on which signals are sampled is not limited to two. Signals may be sampled on three or more capacitors at the same time.

Figure 6:
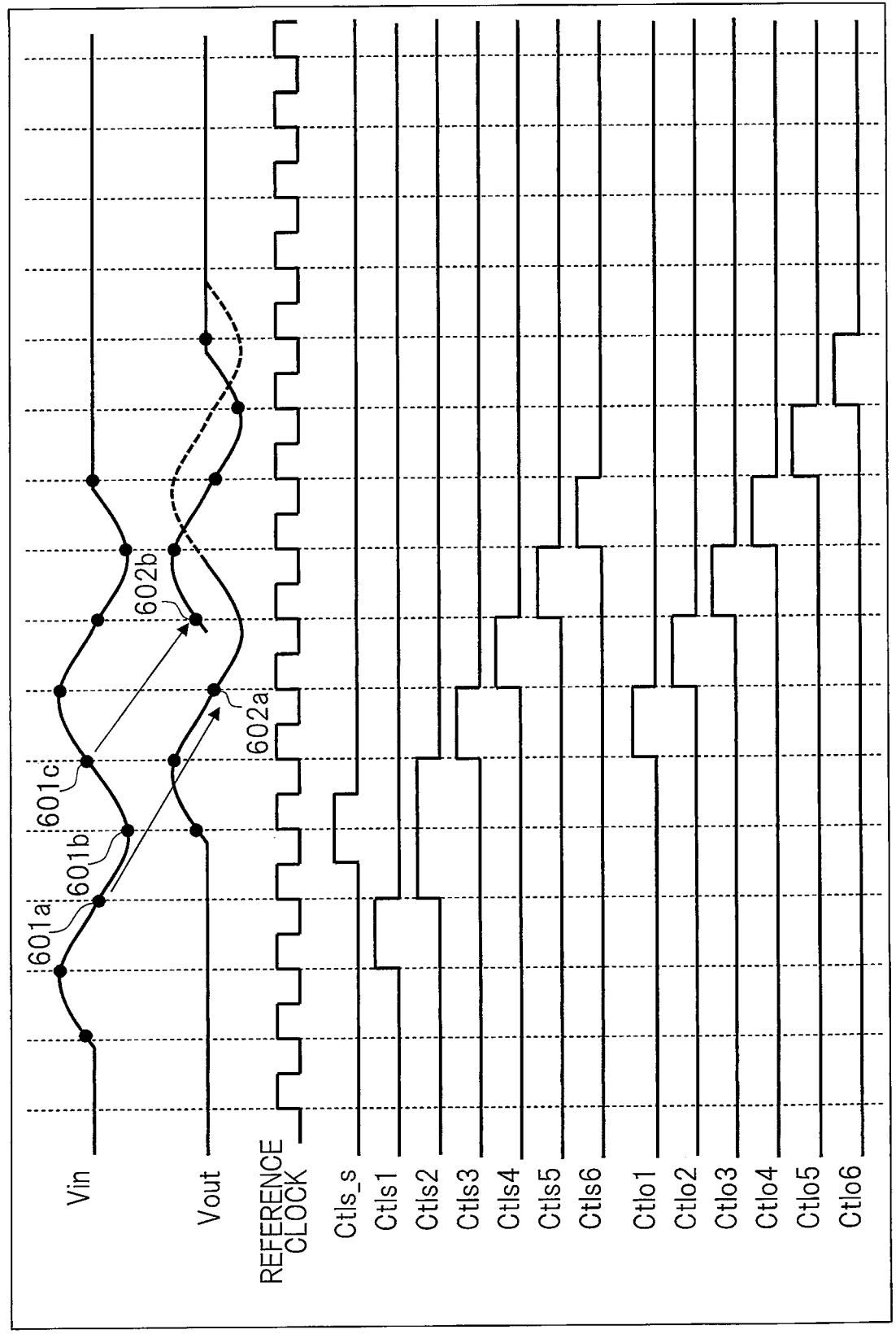
FIG. 6 is a timing chart of an example in decreasing delay time using a write-side control signal in the analog memory unit in FIG. 3.

FIG. 6 is a timing chart of an example in decreasing delay time using the write control signals Ctls in the analog memory unit 205 in FIG. 3.

From the upper side to the lower side, FIG. 6 shows signal timings for the analog input signal Vin inputted to the analog memory unit 205, the output signal Vout outputted from the analog memory unit 205, the reference clock, the control signal Ctls_s outputted from the decoder circuit 307, the write control signals Ctls1 to Ctls6, and the read control signals Ctlo1 to Ctlo6.

As described above, in the case of decreasing delay time, delay time is controlled based on the control signal Ctls_s. First, the input signal Vin is sampled on the capacitor 303a at the timing of the write control signal Ctls1 (601a in FIG. 6). After a lapse of a predetermined period of delay time, the sampled signal is outputted at the timing of the read control signal Ctlo1 (602a in FIG. 6).

In the case where the control signal Ctls_s is inputted, the control signal Ctls is controlled to decrease delay time. In other words, in the case where the control signal Ctls_s is inputted, the write control signal Ctls is controlled to increase its pulse duration.

Specifically, for example, the pulse duration of the write control signal Ctls2 is increased to the pulse duration twice the pulse duration of the reference clock. In this case, sampling is controlled at the timing of the write control signal Ctls2. A signal immediately before the falling edge of the write control signal Ctls2 (601c in FIG. 6) is accumulated on the capacitor 303b. The signal accumulated on the capacitor 303b is outputted at the timing of the read control signal Ctlo2 (602b in FIG. 6).

The signal sampled on the capacitor 303c at the timing of the read control signal Ctls3 is outputted at the timing of the read control signal Ctlo3. An increase in the pulse duration of the write control signal Ctls2 based on the control signal Ctls_s allows a decrease in delay time after that, compared with delay time before then. The output of the buffer 301 to be charged on the capacitor 303 is turned to a voltage output. This can prevent the increased pulse duration from affecting the characteristics.

Figure 7:
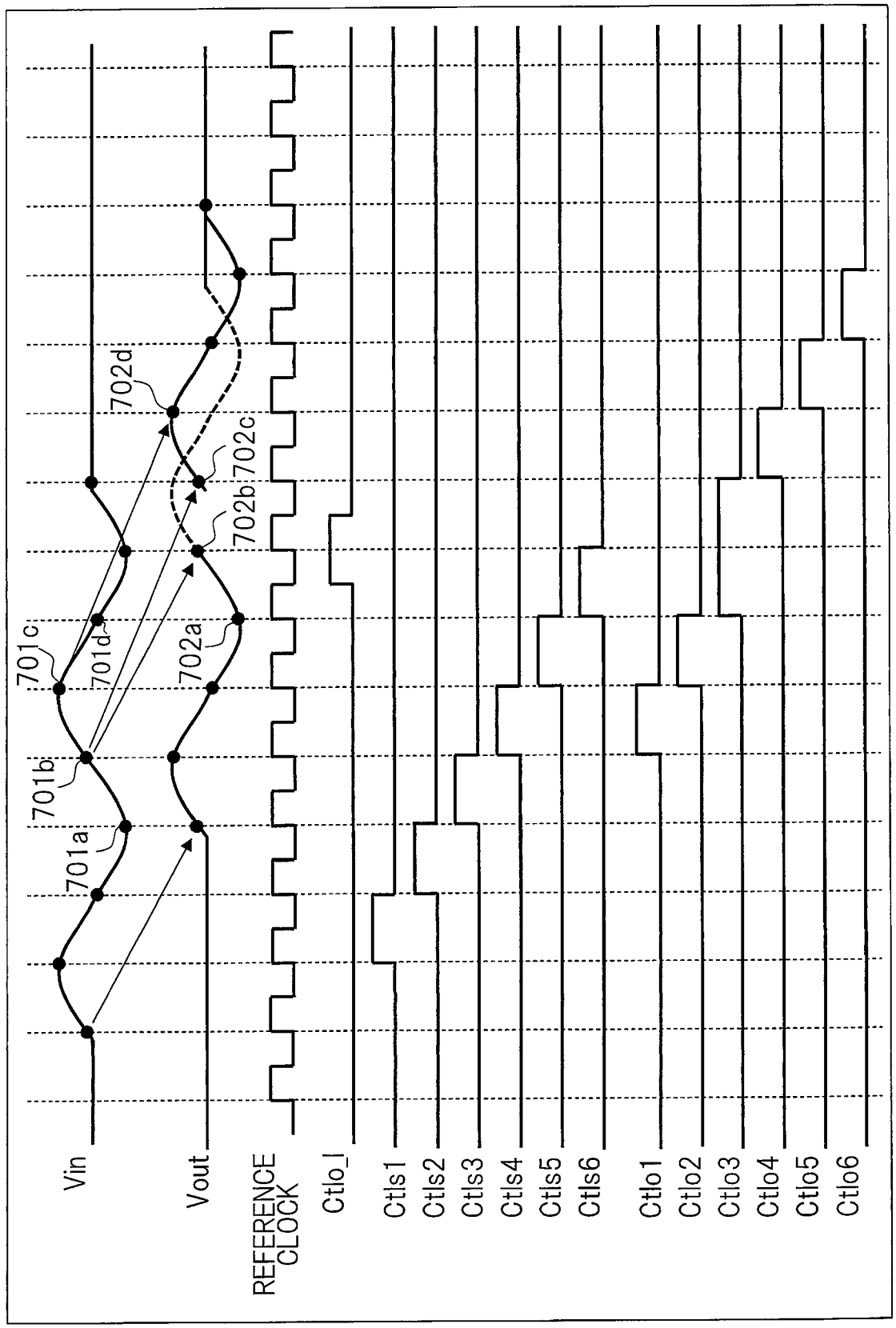
FIG. 7 is a timing chart of an example in increasing delay time using a read-side control signal in the analog memory unit in FIG. 3.

FIG. 7 is a timing chart of an example in increasing delay time using the read control signals Ctlo in the analog memory unit 205 in FIG. 3.

From the upper side to the lower side, FIG. 7 shows signal timings for the analog input signal Vin inputted to the analog memory unit 205, the output signal Vout outputted from the analog memory unit 205, the reference clock, the control signal Ctlo_l outputted from the decoder circuit 307, the write control signals Ctls1 to Ctls6, and the read control signals Ctlo1 to Ctlo6.

In the case where the read control signals Ctlo are changed to increase delay time, delay time is controlled based on the control signal Ctlo_l. The input signal Vin is sampled on the capacitor 303b at the timing of the write control signal Ctls2 (701a in FIG. 7).

After a lapse of a predetermined period of delay time, the sampled signal is outputted at the timing of the control signal Ctlo2 (702a in FIG. 7). The input signal Vin is sampled on the capacitor 303c at the timing of the write control signal Ctls3 (701b in FIG. 7).

In the case where the control signal Ctlo_l is inputted, the control signal Ctlo is controlled to increase delay time. In other words, in the case where the control signal Ctlo_l is inputted to the read control signal generator circuit 306, the control signal Ctlo is controlled to increase its pulse duration.

Specifically, for example, the pulse duration of the read control signal Ctlo3 is increased to the pulse duration about twice the pulse duration of the reference clock. In this case, the signal accumulated on the capacitor 303c is outputted at the timing of the read control signal Ctlo3. However, the output time of the accumulated signal is time that is two reference clocks (702b and 702c in FIG. 7).

Thus, the same data can be outputted for a plurality of samples. The circuit in the subsequent stage is formed in a circuit that receives signals at high impedance and samples signals for a plurality of times in synchronization with the reference clock. Consequently, signals for a plurality of samples can be outputted.

As described above, the pulse duration of the read control signal Ctlo3 is increased based on the control signal Ctlo_l. Thus, delay time after that, compared with delay time before then.

Figure 8:
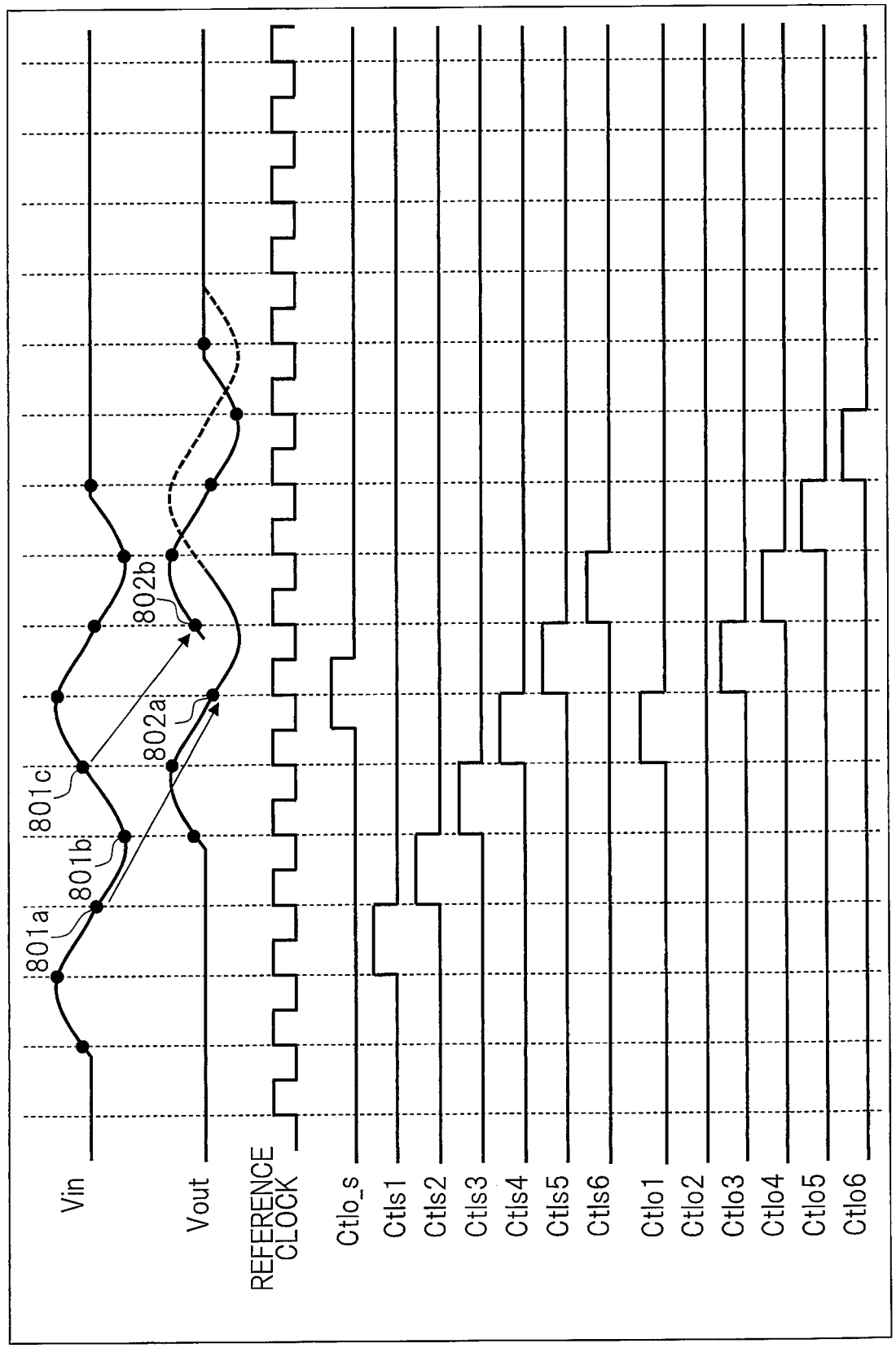
FIG. 8 is a timing chart of an example in decreasing delay time using a read-side control signal in the analog memory unit in FIG. 3.

FIG. 8 is a timing chart of an example in decreasing delay time using the read control signals Ctlo in the analog memory unit 205 in FIG. 3. The signals in FIG. 8 are similar to the ones in FIG. 7, omitting the description.

In the case where the read control signals Ctlo are changed to decrease the delay time, delay time is controlled based on the control signal Ctlo_s. The input signal Vin is sampled on the capacitor 303a at the timing of the write control signal Ctls1 (801a in FIG. 8).

After a lapse of a predetermined period of delay time, the sampled signal is outputted at the timing of the read control signal Ctlo1 (802a in FIG. 8). At the timings of the write control signals Ctls2 and Ctls3, the input signal Vin is sampled on the capacitors 303b and 303c (801b and 801c in FIG. 8).

In the case where the control signal Ctlo_l is inputted to the read control signal generator circuit 306, delay time is controlled to decrease. In other words, in the case where the control signal Ctlo_l is inputted to the read control signal generator circuit 306, one output of the read control signal Ctlo is skipped, and then the subsequent read control signal is turned on.

Specifically, the read control signal generator circuit 306 outputs the read control signal Ctlo3 without outputting the read control signal Ctlo2. In this case, the signal accumulated on the capacitor 303b is not outputted as an output signal. At the timing of the read control signal Ctlo2, the signal accumulated on the capacitor 303c is outputted.

Thus, sampled data is outputted as one item of the sampled data is skipped. In the case where the read control signal Ctlo is controlled, simultaneous reading of signals out of the capacitors 303 at the same time causes outputs to overlap with each other, resulting in unexpected data. Thus, even in the case where delay time is changed, the read control signal Ctlo is controlled so as not to simultaneously read data stored on the capacitors 303.

Figure 9:
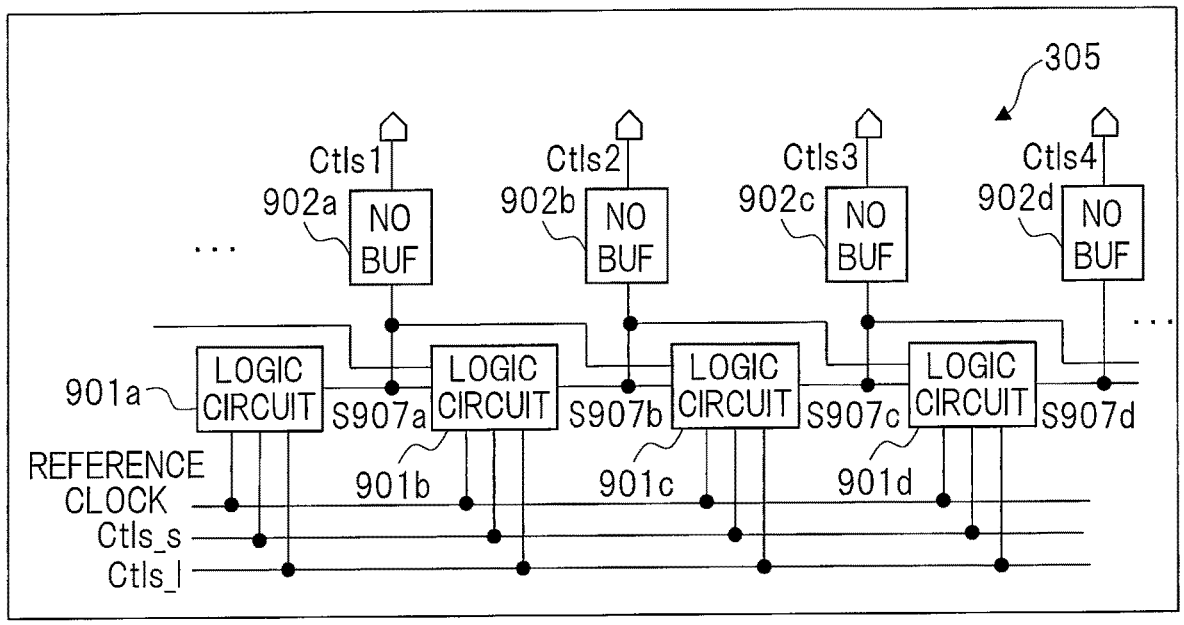
FIG. 9 is a block diagram of an exemplary write control signal generator circuit in FIG. 3.

FIG. 9 is a block diagram of an example of the write control signal generator circuit 305 in FIG. 3.

As illustrated in FIG. 9, the write control signal generator circuit 305 is configured of logic circuits 901a, 901b, 901c, ..., and non-overlapping buffers (in FIG. 9, written in NOBUF) 902a, 902b, 902c, ....

The logic circuits 901a, 901b, 901c, ... each receive the reference clock and the control signals Ctls_s and Ctls_l, and output the read control signals Ctls1, Ctls2, Ctls3, ..., respectively, based on them.

Figure 10:
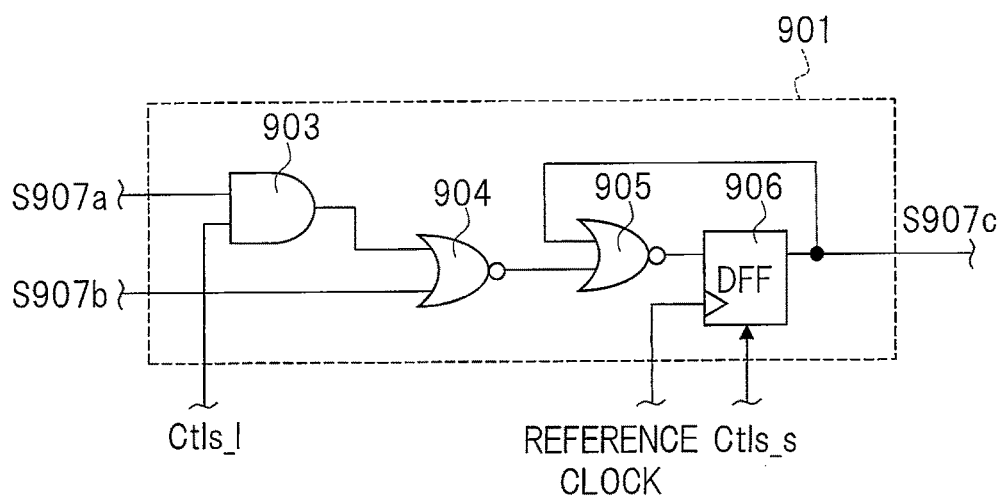
FIG. 10 is an illustration of an exemplary circuit configuration of a logic circuit in FIG. 9.

FIG. 10 is an illustration of an exemplary circuit configuration of the logic circuit 901c in FIG. 9.

Note that, FIG. 10 shows the circuit configuration of the logic circuit 901c, which is a representative one. The configurations are similar in the other logic circuit 901.

The logic circuit 901c includes an AND circuit 903, which is an AND circuit, NOR circuits 904 and 905, which are NOR circuits, and a flip-flop 906.

In the basic operation of the logic circuit 901, the flip-flop 906 outputs the inputted signal with a delay of one clock.

In the case where delay time is not dynamically changed, control signals with high-level output are moved in the order of the write control signals Ctls1, Ctls2, Ctls3, .... In the case where the control signal Ctls_l at high level is inputted, the NOR of the outputs of the logic circuit in the previous stage and the logic circuit in the second previous stage is found, and reflected on the input of the flip-flop 906.

As described above, high level signals are outputted at the same time from two successive logic circuits 901. In the case where the control signal Ctls_s at high level is inputted, the output of the flip-flop 906 is held. This increases the pulse duration for which the write control signal Ctls is outputted.

The output of the logic circuit 901 is outputted as the write control signal Ctls through the NOBUF 902. The NOBUF 902 is a circuit that provides a non-overlapping period in order to prevent the switches 302 from being turned on at the same time when the write control signal Ctls is switched in sampling the signal on the capacitor 303. The NOBUF 902 controls the switch 302 using signals with no overlapping periods.

The use of the write control signal generator circuit 305 in this configuration can generate the write control signal Ctls that dynamically changes delay time.

Figure 11:
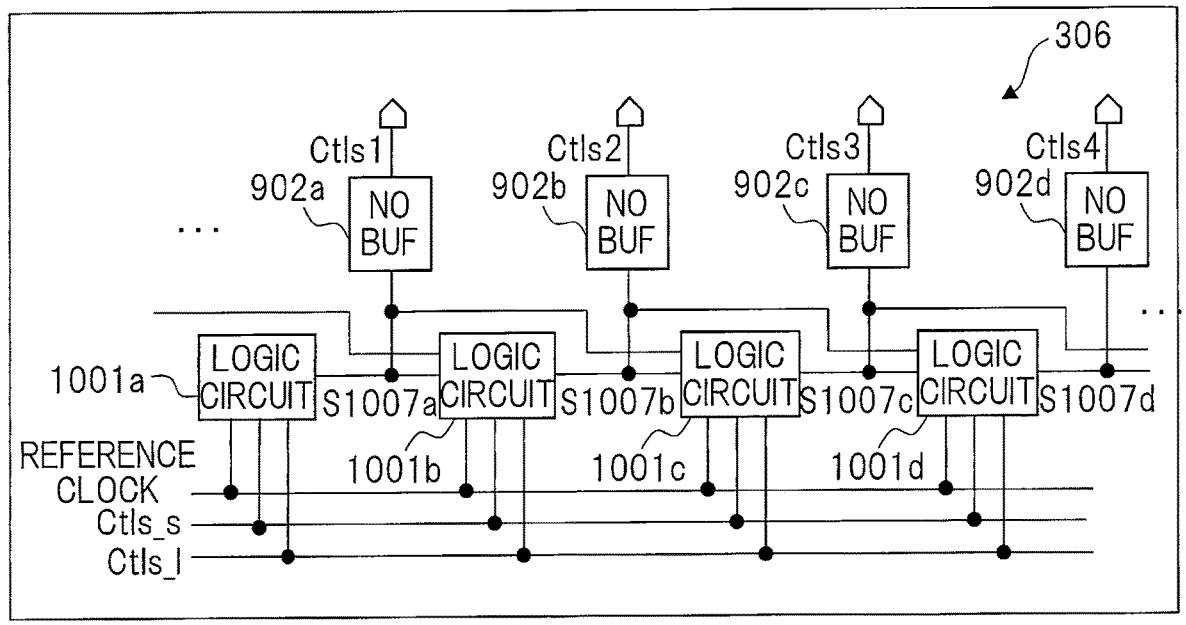
FIG. 11 is a block diagram of an exemplary read control signal generator circuit in FIG. 3.

FIG. 11 is a block diagram of an example of the read control signal generator circuit 306 in FIG. 3.

As illustrated in the drawing, the read control signal generator circuit 306 is configured of logic circuits 1001a, 1001b, 1001c, . . . , and non-overlapping buffers (in FIG. 11, referred to as NOBUF) 1002a, 1002b, 1002c.

The logic circuits 1001, each receive the reference clock and the control signals Ctlo_s and Ctlo_l, and output the read control signals Ctlo1, Ctlo2, Ctlo3, . . . , respectively.

Figure 12:
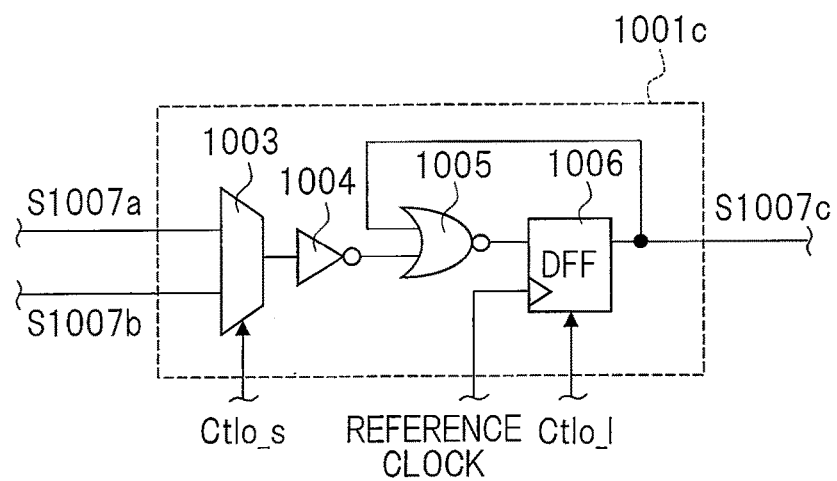
FIG. 12 is an illustration of an exemplary circuit configuration of a logic circuit in FIG. 11.

FIG. 12 is an illustration of an exemplary circuit configuration of the logic circuit 1001c in FIG. 11.

Note that, FIG. 12 also shows the circuit configuration of the logic circuit 1001c, which is a representative one. However, the configuration is similar in the other logic circuits 1001.

As illustrated in the drawing, the logic circuit 1001c includes a selector 1003, an inverter 1004, a NOR circuit 1005, which is a NOR circuit, and a flip-flop 1006.

In the basic operation of the logic circuit 1001, flip-flop 1006 outputs the inputted signal with a delay of one clock.

In the case where delay time is not dynamically changed, control signals at high level output are moved in the order of the read control signals Ctlo1, Ctlo2, Ctlo3, . . . . Based on the voltage level of the control signal Ctlo_s or the polarity, the output of the logic circuit in the previous stage 1001, which is inputted to the selector 1003, or the output of the logic circuit 1001 in the second previous stage is selected.

In the case where delay time is decreased, the control signal Ctlo_s at high level is inputted, and the output of the logic circuit 1001 in the second previous stage is selected. The output of the read control signal Ctlo is an output that one read control signal is skipped.

In the case where the control signal Ctlo_l at high level is inputted, the output of the flip-flop 1006 is held to increase the pulse duration for which the read control signal Ctlo is outputted.

The output of the logic circuit 1001 is outputted as the read control signal Ctlo through the NOBUF 1002.

The use of the read control signal generator circuit 306 in this configuration can generate the read control signal Ctlo that dynamically changes delay time.

As described above, control data for changing delay time is sent from the main device 106 in FIG. 1 to the digital circuit 105 of the probe 100, processed, e.g. decoded, at the decoder circuit 307 of the digital circuit 105 in FIG. 3, as necessary, and then delivered to the write control signal generator circuit 305 and the read control signal generator circuit 306 in FIG. 3.

As described above, delay time can be increased by writing the same data on the capacitors 303 or by increasing the read time of a part of the capacitors 303. Alternatively, delay time can be decreased by increasing the write time of some of the capacitors 303 or by skipping reading data out of some of the capacitors 303.

As described above, delay time is switched among the capacitors on the same line by controlling data write and data read. Thus, delay time can be switched using only the analog memory unit 205. Consequently, delay time can be dynamically changed using a circuit whose area is small.

The output of the delay circuit configured of the analog memory unit 205 is added at the adder circuit 103 in FIG. 2, and sent to the main device 106 through a buffer, for example, not shown. In the main device 106, signals from the probe 100 are received at the analog front end circuit 107 in FIG. 1.

The analog front end circuit 107 is configured of a low-noise amplifier, a programmable gain amplifier, an antialiasing filter, an Analog to Digital Converter (ADC), and other components, not shown. The analog front end circuit 107 amplifies, filters, and converts signals from the probe 100 into digital signals.

Clocks used for sampling signals at the analog to digital converter are clocks generated from the same oscillator source for the reference clock sent from the main device 106 to the probe 100, for example.

The output of the delay circuit of the single-element circuits 102 of the subarray 101 is outputted in synchronization with the reference clock. Thus, also in the analog to digital converter, signals are converted into digital signals in synchronization with the reference clock.

Note that, a clock that the reference clock is multiplied or divided may be used as necessary. Taking into account of delay time on cables, phases for analog to digital conversion may be shifted.

In the analog memory unit 205 of the probe 100, signals are outputted in synchronization with the reference clock. This causes spike noise at the leading edge and trailing edge of the reference clock.

Signals are sampled at the analog to digital converter of the main device 106 in synchronization with the reference clock. Thus, signals can be digitized as noise on the edges of the clock is avoided. The signals digitized at the analog to digital converter are subjected to signal processing, e.g. digital phasing, and then ultrasound images are displayed.

Note that, in the first embodiment, the configuration is described in which a capacitor is used for an element that stores analog signals, and electric charges accumulated on the capacitor are used to store the analog signal, although any configuration is possible.

For example, a transistor such as a MOS (Metal Oxide Semiconductor) may be used to store analog signals as electric currents. In the case where analog signals are stored as electric currents, power consumption is increased, on one hand, whereas a merit is a reduction in its occupied area, on the other hand, compared with the case of the capacitor.

Note that, in the adder circuit 103 in FIG. 2, it is unnecessary to add all the outputs of the single-element circuits 102. Alternatively, a configuration may be possible in which the adder circuit 103 is split into a plurality of blocks and signals are added at each block. For example, in the case where 192 channels are provided, i.e. 192 single-element circuits 102 are provided, a configuration may be possible in which signals are added for four channels each and 48 outputs are obtained after added. Alternatively, for example, a configuration may be possible in which for the signals of the single-element circuits 102 in 8,192 channels, 64 channels of signals in an 8×8 array are each added and 128 outputs are obtained. These signals are coupled from the probe 100 to the main device 106 via cables for transmission.

A configuration may be possible in which a low-pass filter is provided for the output signal of each of the analog memory units 205. For example, in the case where this filter is a filter that can remove the noise of the clock cycle, the noise of the clock cycle can be reduced. A similar low-pass filter may be provided for the output of the adder circuit 103.

A capacitor for controlling bandwidths may be connected to the output of the reception analog front end unit 204.

As described above, signals in a plurality of channels are delayed and added, allowing a decrease in the number of output signals for the number of the elements of the transducers. Thus, the number of cables can be decreased, and the number of the analog to digital converters for converting analog signals into digital signals can be decreased, allowing a cost reduction.

In the two-dimensional transducer array, coupling signals in all the channels from the probe to the main body is impractical. However, as in the embodiment, signals are highly accurately delayed and added, allowing connection from the probe to the apparatus main body with a practical number of cables. Dynamically changing delay time can provide received data more in focus.

This allows the implementation of a compact ultrasound imaging apparatus. Consequently, the costs of the ultrasound imaging apparatus can be decreased.

The write control signal Ctls and the read control signal Ctlo are generated at the digital circuit 105, and coupled to the single-element circuits 102a, 102b, . . . . The control signals may be coupled to the single-element circuits 102 through separate interconnections, or may be coupled in common connections.

Specifically, for example, delay time is given by the difference between the write control signal Ctls and the read control signal Ctlo. Thus, the write or read control signal may be shared among all the single-element circuits. In the case where the read control signal Ctlo is shared among the single-element circuits, the write control signal Ctls is changed in each of the single-element circuits, and the single-element circuits generate different periods of delay time. The shared control signal can reduce the number of interconnections, and the area of the circuit can be made small.

Alternatively, a configuration may be possible in which for the single-element circuits two-dimensionally disposed, the write control signal Ctls is shared in the direction of the long side, for example, and the read control signal is shared in the direction of the short side. In this case, the number of interconnections to be connected to the single-element circuits can be decreased, and the area of the circuit can be made small.

In the embodiment, the use of any of the write control signal and the read control signal can increase or decrease delay time. Thus, even in the case where the interconnections are shared as described above, selecting any one of the write control signal and the read control signal can dynamically change delay time.

Note that, in the first embodiment, the configuration is described in which the analog memory unit 205 that is the delay circuit is provided on the reception-side circuit. However, the delay circuit may be used on the transmission-side circuit. Alternatively, a configuration may be possible in which the delay circuit is shared between the transmission-side circuit and the reception-side circuit, and the delay circuit is switched between in transmission and in reception.

Second Embodiment

As illustrated in FIG. 3, in the first embodiment, the circuit configuration is described in which in the analog memory unit 205, analog signals are accumulated on the capacitor 303 connected to the ground (the reference potential VSS). However, for the configuration of the analog memory unit 205, any configuration is possible.

Therefore, in a second embodiment, another configuration of the analog memory unit 205 will be described.

For another configuration of the analog memory unit 205, many circuit configurations can be designed, including, for example, circuit configurations in which analog signals are charged on the capacitor connected to the artificial ground of an operational amplifier, not to the ground, in which a differential circuit is used, not a single-ended circuit, and in which a reset period is provided.

A closed loop circuit is formed, not an open loop circuit. This allows the improvement of the accuracy of the output voltage.

Figure 13:
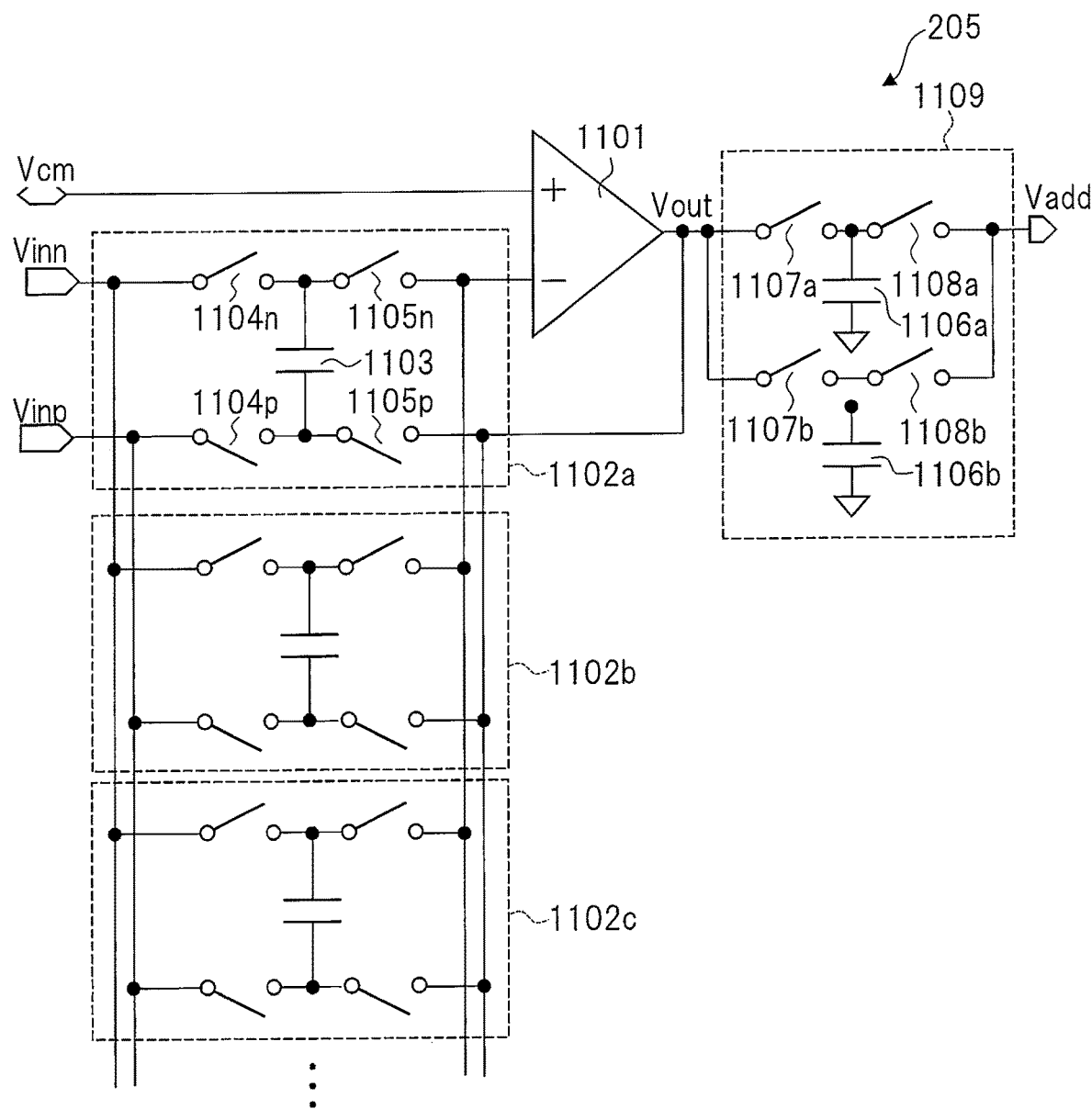
FIG. 13 is an illustration of an exemplary circuit configuration of an analog memory unit and an adder circuit according to a second embodiment.

FIG. 13 is an illustration of an exemplary circuit configuration of the analog memory unit 205 and the adder circuit 103 according to the second embodiment.

As illustrated in FIG. 13, the analog memory unit 205 is configured of an operational amplifier 1101 and switch-capacitor units 1102a, 1102b, . . . . The adder circuit 103 is configured of a plurality of electric charge adding units 1109. The switch-capacitor unit 1102 is configured of a capacitor 1103, and switches 1104p, 1104n, 1105p, and 1105n.

Here, subscripts p and n of the switches express the positive side and negative side of the differential circuit, and are sometimes omitted unless otherwise specified. The electric charge adding unit 1109 is configured of capacitors 1106a and 1106b, and switches 1107a, 1107b, 1108a, and 1108b.

The analog memory unit 205 is a circuit, in which the switch-capacitor units are connected in parallel with each other and signals are sampled and accumulated, and then outputted after a lapse of a predetermined period of delay time. Here, the differential signals Vinp and Vinn are signals outputted from the reception analog front end unit 204. A voltage Vcm inputted to the positive (+) input part of the operational amplifier 1101 is a reference voltage.

Figure 14:
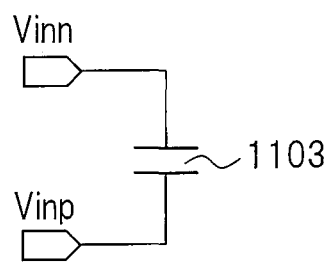
FIG. 14 is an illustration of an exemplary equivalent circuit in sampling at a switch-capacitor unit of the analog memory unit in FIG. 13.
Figure 15:
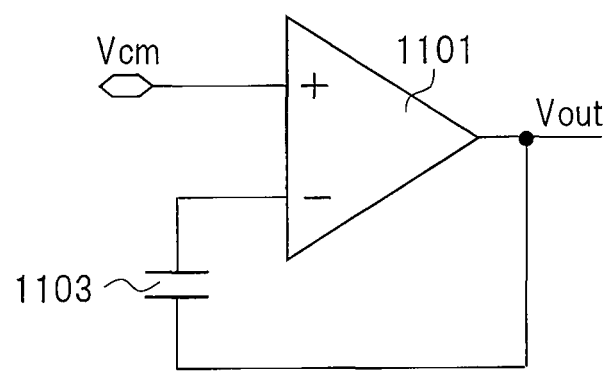
FIG. 15 is an illustration of an exemplary equivalent circuit in holding at the switch-capacitor unit of the analog memory unit in FIG. 13.

FIG. 14 is an illustration of an exemplary equivalent circuit in sampling signals at the switch-capacitor unit 1102 of the analog memory unit 205 in FIG. 13. FIG. 15 is an illustration of an exemplary equivalent circuit in holding signals at the switch-capacitor unit 1102 of the analog memory in FIG. 13.

In sampling signals, the switch 1104 is turned on, and the switch 1105 is turned off. Thus, the capacitor 1103 is connected across the inputted differential signals, and electric charges corresponding to the inputted differential signals are accumulated on the capacitor 1103.

After a lapse of a predetermined period of delay time and then outputting accumulated data, the switch 1105 is turned on. The capacitor 1103 and the operational amplifier 1101 configure a feed-back circuit. In sampling signals, a signal corresponding to the electric charges accumulated on the capacitor 1103 is outputted as the output signal Vout.

The output signal Vout, which is delayed and then outputted, is accumulated as electric charges at the electric charge adding unit 1109 of the adder circuit 103. The electric charge adding unit 1109 is operated at a clock in a period twice the period of the reference clock, for example. In the first phase, the switch 1107a is turned on, the switch 1108a is turned off, and a signal corresponding to the output signal Vout is accumulated as electric charges on the capacitor 1106a. At the same time, the switch 1107b is turned off, the switch 1108b is turned on, and the electric charges accumulated on the capacitor 1106b are outputted to a terminal Vadd connected to the input part of the buffer 104 in FIG. 1.

In the second phase, the switch 1107a is turned off, the switch 1108a is turned on, and the electric charges accumulated on the capacitor 1106a are outputted to the terminal Vadd connected to the input part of the buffer 104 in FIG. 1.

At the same time, the switch 1107b is turned on, the switch 1108b is turned off, and a signal corresponding to the output signal Vout is accumulated as electric charges on the capacitor 1106b. As described above, the operation is repeatedly performed in which the signal Vout delayed in two phases is accumulated as electric charges and then outputted.

A signal is outputted as electric charges as described above. Thus, in the adder circuit 103, in adding the output signals of the single-element circuits 102, only the direct connection of the interconnections to each other averages electric charges and adds signals. Only the connection of the interconnections allows signals to be added with no use of a special adder circuit. Consequently, the area of the circuit can be made small.

The control signal that operates the switches of the electric charge adding unit 1109 causes the sampling of signals immediately before the switch 1105, which outputs a delayed signal, is changed from on to off. The provision of such timing allows the elimination of noise produced in switching and the accurate sampling of signals.

Delay time is determined based on the time difference between the control signal of the switch 1104 that determines the timing of sampling signals on the capacitor and the control signal of the switch 1105 that determines the timing of outputting signals from the capacitor.

For the control signal of the switch 1104, the write control signals Ctls1, Ctls2, . . . , which are described in the first embodiment, are used. For the control signal of the switch 1105, the read control signals Ctlo1, Ctlo2, . . . are used. In dynamically changing delay time, delay time is increased or decreased by changing the control signals Ctls and Ctlo.

As in the embodiment, the input signal is sampled as the differential signal on the capacitor. Thus, the analog signal can be highly accurately sampled and delayed. Specifically, forming the differential circuit can reduce distortion. The configuration of a closed loop circuit with the operational amplifier for holding sampled signals allows highly accurate signals to be obtained.

Delay time is provided for the control signal that controls the switches. Thus, the analog signal can be delayed. The control signal is dynamically changed. Thus, delay time can be dynamically changed.

Electric charges are repeatedly accumulated and outputted in the unit of the reference clock at the electric charge adding unit 1109. Thus, even in the case where the pulse duration of the read control signal is increased, output in synchronization with the reference clock can be obtained.

Figure 16:
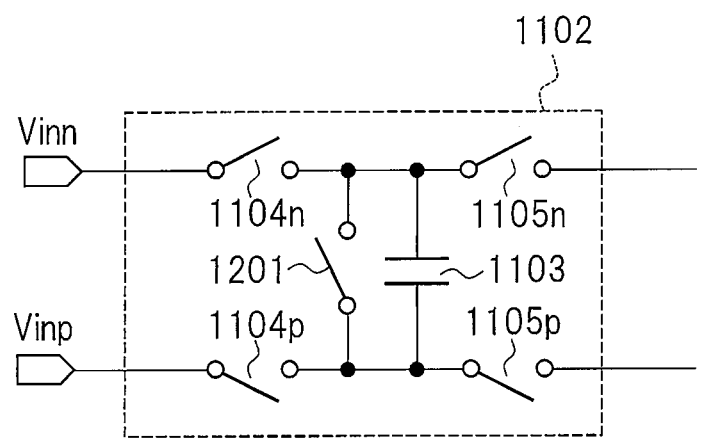
FIG. 16 is an illustration of another exemplary configuration of the switch-capacitor unit of the analog memory unit in FIG. 13.

FIG. 16 is an illustration of another exemplary configuration of the switch-capacitor unit 1102 of the analog memory unit 205 in FIG. 13.

As illustrated in FIG. 16, in this case, the switch-capacitor unit 1102 is configured of the capacitor 1103, the switches 1104p, 1104n, 1105p, and 1105n, and a switch 1201. Compared with the configuration illustrated in FIG. 13, the switch 1201 is newly added. The switch 1201 is used as a reset switch.

The write control signal Ctls is inputted to the control terminals of the switches 1104p and 1104n. The read control signal Ctlo is inputted to the control terminals of the switches 1105p and 1105n. A reset control signal Ctlr is inputted to the control terminal of the switch 1201.

Thus, the write control signal Ctls controls the turning on/off of the switches 1104p and 1104n. The read control signal Ctlo controls the turning on/off of the switches 1105p and 1105n. The reset control signal Ctlr controls the turning on/off of the switch 1201.

In accumulating data on the capacitor 1103, electric charges to be accumulated are changed depending on the initial state. Thus, desirably, the capacitor is reset before accumulating data or after outputting data.

In the case where delay time is not dynamically changed, the timing of sampling signals and the timing of outputting signals are fixed and periodic. Thus, the capacitor only has to be periodically reset.

Specifically, conditions are given that the write control signal and the read control signal for the nth capacitor are a write control signal Ctls<n> and a read control signal Ctlo<n>, respectively, and a signal to operate the switch 1201 is a reset control signal Ctlr<n>.

In this case, for the reset control signal Ctlr<n>, a write control signal Ctls<n−1> for the previous capacitor only has to be used. Alternatively, a read control signal Ctlo<n+1> for the next capacitor only has to be used.

As in the first embodiment described above, in the case where delay time is dynamically changed, the write control signal or the read control signal is not allowed to be used for the reset control signal as they are. Therefore, a technique for generating the reset control signal will be described in the case where delay time is dynamically changed.

Figure 17:
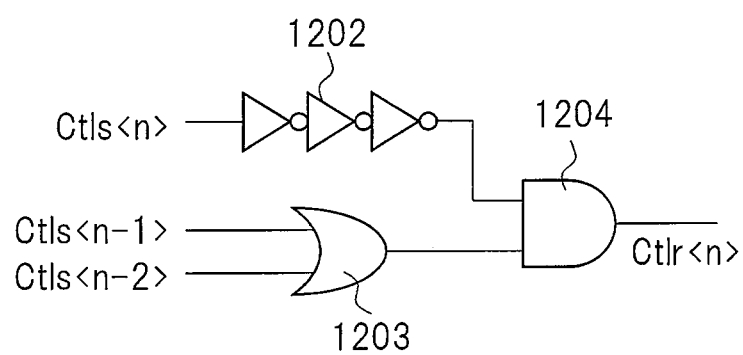
FIG. 17 is an illustration of an exemplary reset control signal generator circuit that generates a reset control signal to operate a reset switch of the switch-capacitor unit in FIG. 16.

FIG. 17 is an illustration of an exemplary reset control signal generator circuit that generates a reset control signal to operate the reset switch 1201 of the switch-capacitor unit 1102 in FIG. 16.

The reset control signal generator circuit is a circuit that generates reset control signals using the write control signal. For example, the reset control signal generator circuit is provided on the analog memory unit 205. As illustrated in FIG. 17, the reset control signal generator circuit is configured of an inverter delay unit 1202, an OR circuit 1203, which is an OR circuit, and an AND circuit 1204, which is an AND circuit.

The inverter delay unit 1202 is configured of a plurality of inverters in series connection. The write control signal Ctls<n> is inputted to the input part of the inverter delay unit 1202. One input part of the AND circuit 1204 is connected to the output part of the inverter delay unit 1202.

One input part of the OR circuit 1203 is connected to receive the previous write control signal Ctls<n−2>. The other input part of the OR circuit 1203 is connected to receive a second previous write control signal Ctls<n−1>.

The other input part of the AND circuit 1204 is connected to the output part of the OR circuit 1203. From the output of the AND circuit 1204, the reset control signal Ctlr<n> is outputted.

Figure 18:
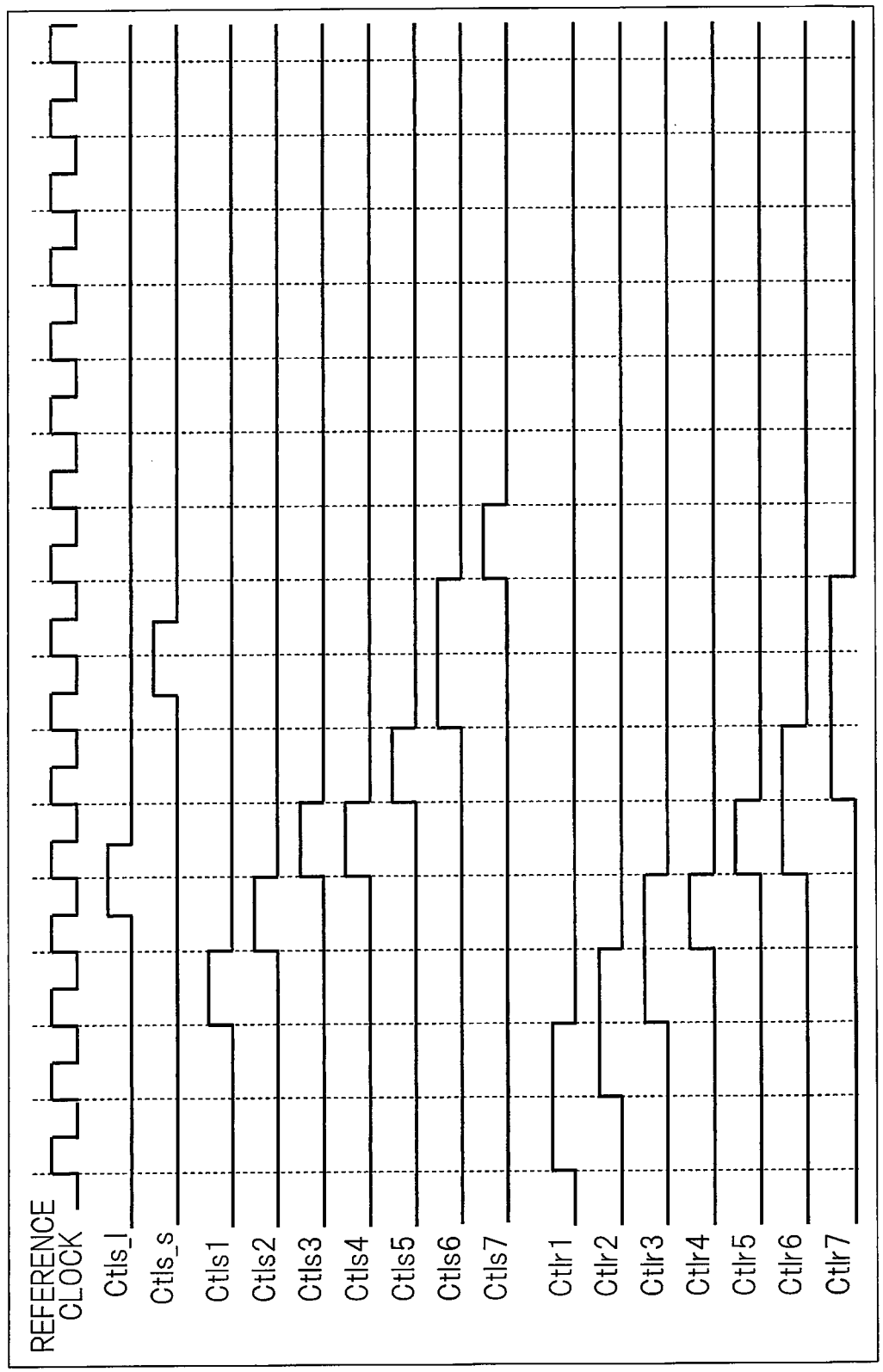
FIG. 18 is a timing chart of exemplary signal timings for the components of the reset control signal generator circuit in FIG. 17.

FIG. 18 is a timing chart of exemplary signal timings for the components of the reset control signal generator circuit in FIG. 17.

From the upper side to the lower side, FIG. 18 shows signal timings for the reference clock, the control signals Ctls_l and Ctls_s, write control signals Ctls1 to Ctls7, and read control signals Ctlr1 to Ctlr7.

First, in order to reset data before signals are sample on the capacitor, the control signal Ctls<n−1> in the previous stage and the control signal Ctls<n−2> in the second previous stage are ORed.

In dynamically changing delay time, the control signals Ctls<n> and Ctls<n−1> are sometimes simultaneously turned to high level. Thus, the control signal Ctls<n> is inverted at the inverter delay unit 1202, and ANDed with the output of the OR circuit 1203 for generating the reset control signal Ctlr<n>. This is because in the state in which the control signal Ctls<n> is at high level, the input signal Vin has to be sampled, and thus the reset switch 1201 must not be turned on.

In order to guarantee that the reset switch 1201 is not turned on after the switch 1104 is controlled to sample signals, the control signal Ctls<n> is delayed at the inverter delay unit 1202. This can prevent glitches, and can hold sampled electric charges.

Figure 19:
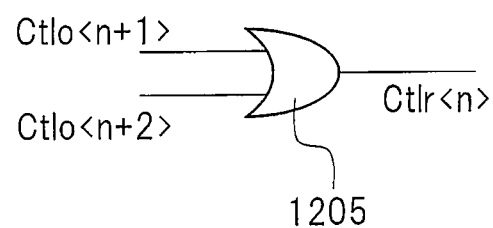
FIG. 19 is an illustration of another exemplary reset control signal generator circuit in FIG. 17.

FIG. 19 is an illustration of another exemplary reset control signal generator circuit in FIG. 17.

In this case, the reset control signal generator circuit generates the reset control signal using the read control signal. As illustrated in FIG. 19, the reset control signal generator circuit is configured of an OR circuit 1205.

Figure 20:
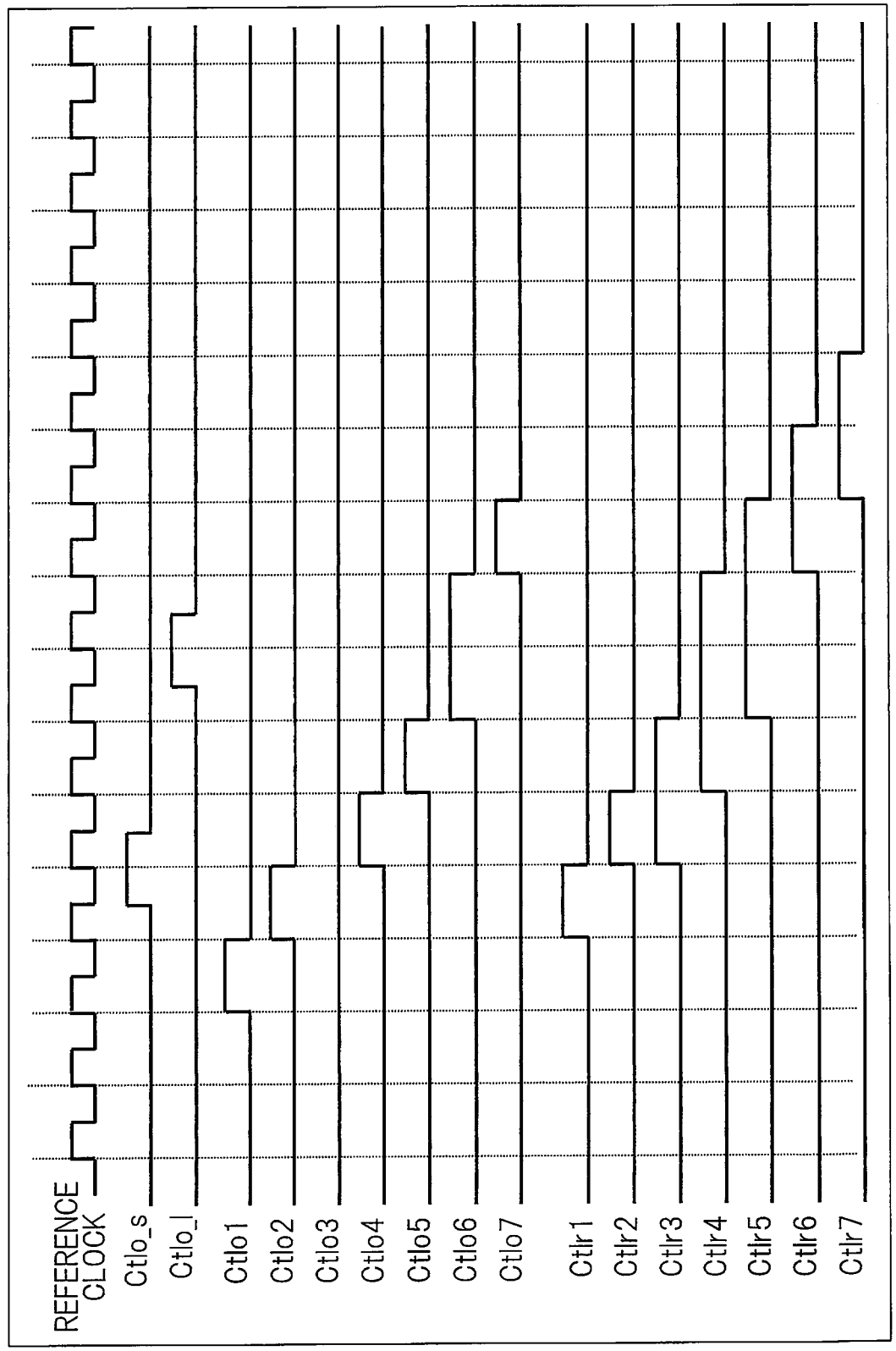
FIG. 20 is a timing chart of exemplary signal timings for the components of the reset control signal generator circuit FIG. 19.

FIG. 20 is a timing chart of an example of signal timings for the components of the reset control signal generator circuit in FIG. 19.

From the upper side to the lower side, FIG. 20 shows signal timings for the reference clock, the control signals Ctlo_l and Ctlo_s, the write control signals Ctls1 to Ctls7, and the read control signals Ctlr1 to Ctlr7.

In this case, the reset control signal generator circuit in FIG. 20 resets data stored on the capacitor after data sampled on the capacitor is outputted. Specifically, the reset control signal generator circuit ORs a read control signal Ctlo<n+1> in the next stage and a read control signal Ctlo<n+2> in the second next stage, and generates the reset control signal Ctlr<n>.

In the case where delay time is dynamically changed, the read control signal Ctlo<n+1> is sometimes not outputted. Thus, it is guaranteed that these two control signals are ORed to reset data as described above.

A simple circuit configuration with merits is a circuit that generates the reset control signal using the read control signals in FIG. 19. On the other hand, in the case where data is reset immediately after sampled data is read, it takes time to again sample signals after resetting. Taking into account of electric charges possibly to be noise accumulated by capacitor coupling, for example, until signals are again sampled, it is desirable to reset data immediately before sampled data is read. In this case, the reset control signal is generated using the write control signals in FIG. 17, which is a merit.

Third Embodiment

In a third embodiment, another configuration of the analog memory unit 205 in FIG. 13 according to the second embodiment will be described.

Figure 21:
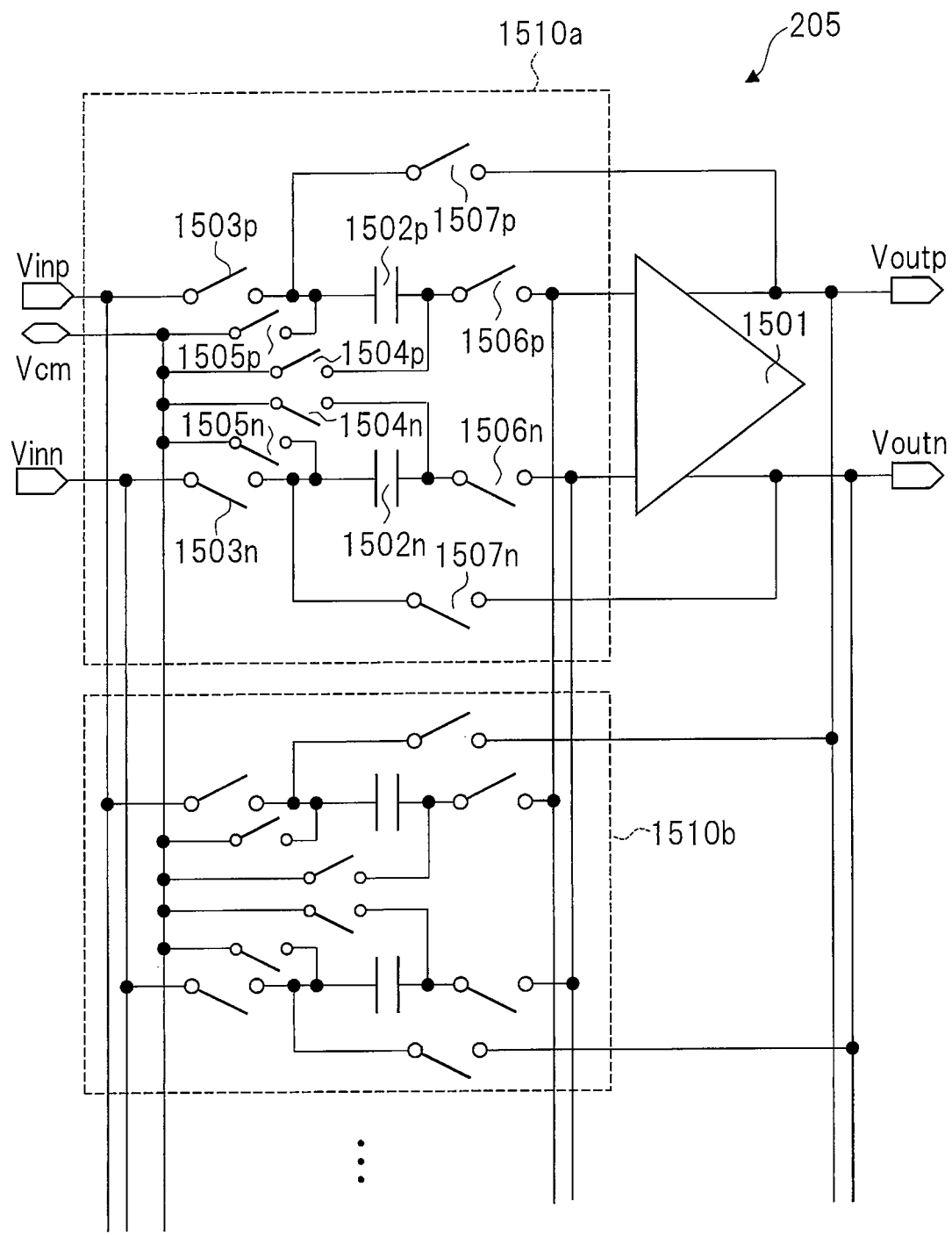
FIG. 21 is an illustration of another exemplary circuit configuration of the analog memory unit in FIG. 13.

FIG. 21 is an illustration of another exemplary circuit configuration of the analog memory unit 205 in FIG. 13.

As illustrated in FIG. 21, the analog memory unit 205 is configured of an operational amplifier 1501 and switch-capacitor units 1510a, 1510b, . . . . The switch-capacitor unit 1510 is configured of capacitors 1502p and 1502n, and switches 1503p, 1503n, 1504p, 1504n, 1505p, 1505n, 1506p, 1506n, 1507p, and 1507n.

Here, subscripts p and n of the switches express the positive side and negative side of the differential circuit, and are sometimes omitted unless otherwise specified. Compared with the circuit according to the second embodiment, the circuit configuration is one that is a fully differential circuit, and the characteristics are strongly resistant to noise in common mode. The differential signals Vinp and Vinn are input signals of differential signals. The common voltage Vcm is a reference voltage.

In the connection of the switch-capacitor unit 1510a, the common voltage Vcm is supplied to one ends of the switches 1504n, 1504p, 1505p, and 1505n, the differential signal Vinp is inputted to one end of the switch 1503p, and the differential signal Vinn is inputted to one end of the switch 1503n.

To the other end of the switch 1503p, one end of the switch 1507p, the other end of the switch 1505p, and one end of the capacitor 1502p are connected. To the other end of the capacitor 1502p, one end of the switch 1506p and the other end of the switch 1504p are connected. To the other end of the switch 1505n, the other end of the switch 1503n, one end of the switch 1507n, and one end of the capacitor 1502n are connected. To the other end of the capacitor 1502n, the other end of the switch 1504n and one end of the switch 1506n are connected.

The other end of the switch 1506p is connected to one input part of the operational amplifier 1501. The other end of the switch 1506n is connected to the other input part of the operational amplifier 1501. The other end of the switch 1507p is connected to one output part of the operational amplifier 1501. The other end of the switch 1507n is connected to the other output part of the operational amplifier.

The one output part of the operational amplifier 1501 is an output terminal to output a differential output signal Voutp. The other output part of the operational amplifier 1501 is an output terminal to output a differential output signal Voutn.

Note that, the connection relationship of the switch-capacitor unit 1510a is described here. The connection relationship of the other switch-capacitor units 1510 is similar.

Figure 22:
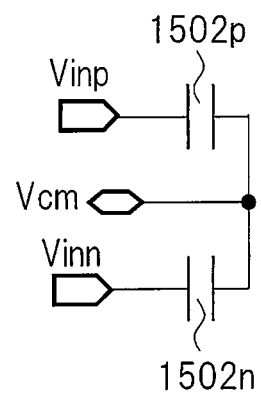
FIG. 22 is an illustration of an exemplary equivalent circuit in sampling at a switch-capacitor unit of the analog memory unit in FIG. 21.
Figure 23:
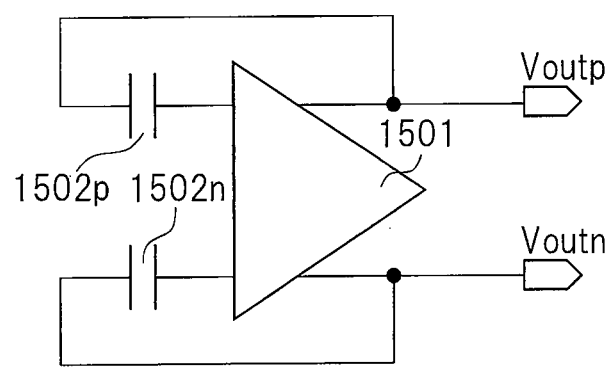
FIG. 23 is an illustration of an exemplary equivalent circuit in holding at the switch-capacitor unit of the analog memory unit in FIG. 21.
Figure 24:
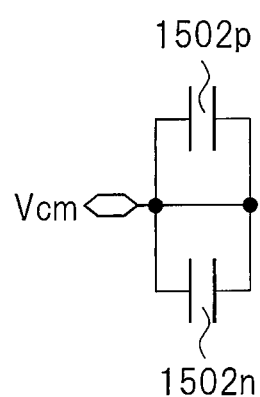
FIG. 24 is an illustration of an exemplary equivalent circuit in resetting the switch-capacitor unit in FIG. 21.

FIG. 22 is an illustration of an exemplary equivalent circuit in sampling signals at the switch-capacitor unit 1510 of the analog memory unit 205 in FIG. 21. FIG. 23 is an illustration of an exemplary equivalent circuit in holding signals at the switch-capacitor unit 1510 of the analog memory in FIG. 21. FIG. 24 is an illustration of an exemplary equivalent circuit in resetting data in the switch-capacitor unit 1510 in FIG. 21.

In sampling signals at the switch-capacitor unit 1510, the switches 1503 and 1504 are turned on, and the switches 1505, 1506, and 1507 are turned off. Thus, the capacitor 1502 is connected across the differential signals Vinp and Vinn and the common voltage Vcm.

In sampling signals, electric charges corresponding to the differential signals Vinp and Vinn are accumulated on the capacitor 1502. In holding signals, the switches 1503, 1504, and 1505 are turned off, and the switches 1506 and 1507 are turned on.

The capacitor 1502 and the operational amplifier 1501 configure a feed-back circuit. In sampling signals, signals corresponding to the electric charges accumulated on the capacitor 1502 are outputted as the differential output signals Voutp and Voutn. In resetting the signals accumulated on the capacitor, the switches 1504 and 1505 are turned on.

Delay time is determined by the time difference between the write control signal for the switch 1504, which determines the timing of sampling signals on the capacitor, and the read control signals for the switch 1506 and the switch 1507, which determine the timing of outputting signals from the capacitor.

For the control signals for the operations of the switch 1503 and the switch 1504, the write control signals Ctls1, Ctls2, . . . , for example, are used, which are shown in the first embodiment. For the control signals for the operations of the switch 1506 and the switch 1507, the read control signals Ctlo1, Ctlo2, ... are used, which are similarly shown in the first embodiment.

The write control signals Ctls1, Ctls2, ..., and the read control signals Ctlo1, Ctlo2, ... are generated at the write control signal generator circuit 305 and the read control signal generator circuit 306, respectively, in FIG. 3.

Similarly to the first embodiment, in dynamically changing delay time, delay time is increased or decreased by changing the control signals Ctls_l, Ctls_s, Ctlo_l and Ctlo_s inputted to the write control signal generator circuit 305 and the read control signal generator circuit 306.

As described above, the switch-capacitor unit 1510 is formed as a circuit for differential input and differential output. Thus, analog input signals can be highly accurately sampled and delayed, and a circuit strongly resistant to noise in common mode can be provided.

As described above, some aspects of the inventions made by the present inventors are described specifically based on the embodiments. It goes without saying that the present invention is not limited to the embodiments and can be variously modified and altered in the scope not deviating from the gist of the present invention.

Note that, the present invention is not limited to the forgoing embodiments, and includes various exemplary modifications. For example, the foregoing embodiments are described in detail for easy understanding of the present invention. The present invention is not necessarily limited to ones including all the described configurations.

A part of the configuration of an embodiment can be replaced by the configuration of another embodiment. The configuration of an embodiment can be added with the configuration of another embodiment. Some of the configurations of the embodiments can be added with, removed from, or replaced by the other configurations.

LIST OF REFERENCE SIGNS

100: probe
101: subarray
102: single-element circuit
103: adder circuit
104: buffer
105: digital circuit
106: main device
107: analog front end circuit
201: transducer
202: transmission reception separator
203: transmitting unit
204: reception analog front end unit
205: analog memory unit
301: buffer
302: switch
303: capacitor
304: switch
305: control signal generator circuit
306: control signal generator circuit
307: decoder circuit
901: logic circuit
902: non-overlapping buffer
903: AND circuit
904: NOR circuit
906: flip-flop
1001: logic circuit
1002: non-overlapping buffer
1003: selector
1004: inverter
1005: NOR circuit
1006: flip-flop
1101: operational amplifier
1102: switch-capacitor unit
1103: capacitor
1104: switch
1105: switch
1106: capacitor
1107: switch
1108: switch
1109: electric charge adding unit
1201: switch
1202: inverter delay unit
1203: OR circuit
1204: AND circuit
1205: OR circuit
1501: operational amplifier
1510: switch-capacitor unit
1502: capacitor
1503: switch
1504: switch
1505: switch
1506: switch
1507: switch

The invention claimed is:

1. An ultrasound probe comprising:
a plurality of transmitter-receiver units that respectively transmit an ultrasonic wave and receive a reflected wave of the ultrasonic wave produced by a difference between acoustic impedances; and
a digital circuit that generates write control signals according to a reference clock and read control signals according to the reference clock,
wherein each of the plurality of transmitter-receiver units respectively includes a delay generator circuit that sequentially accumulates a voltage level corresponding to the reflected wave based on the write control signals and sequentially outputs the accumulated voltage level based on the read control signals,
wherein the delay generator circuit includes:
a plurality of memory elements;
a plurality of first switches that sequentially accumulate the voltage level on the memory elements based on the write control signals; and
a plurality of second switches that sequentially output the voltage level accumulated on the memory elements based on the read control signals, and
wherein the digital circuit controls an output of the write control signals and the read control signals to vary a delay time between the accumulation of the voltage level corresponding to the reflected wave and the output of the voltage level accumulated on the memory elements,
wherein, when a first delay time control signal that increases the delay time is inputted to the digital circuit, the digital circuit generates the write control signals that control the first switches to accumulate a same voltage level on two or more of the memory elements for a same period of the reference clock depending on an input period of the first delay time control signal,
wherein, when a second delay time control signal that increases the delay time is inputted to the digital circuit, the digital circuit generates the read control signals that control the second switches to continue an output period of the voltage level outputted from one of the memory elements for a next period of the reference clock depending on an input period of the second delay time control signal, wherein, when a third delay time control signal that decreases the delay time is inputted to the digital circuit, the digital circuit generates the write control signals that control the first switches to continue an input period in which one of the memory elements accumulates the voltage level for a next period of the reference clock depending on an input period of the third delay time control signal, and wherein, when a fourth delay time control signal that decreases delay time of the reflected wave is inputted to the digital circuit, the digital circuit generates the read control signals that control one or more of the second switches not to output the voltage level from one or more of the memory elements for a next period of the reference clock depending on an input period of the fourth delay time control signal.

2. An ultrasound probe comprising:

a plurality of transmitter-receiver units that respectively transmit an ultrasonic wave and receive a reflected wave of the ultrasonic wave produced by a difference between acoustic impedances, the reflected wave inputted to the delay generator circuit is a differential input signal; and a digital circuit that generates write control signals according to a reference clock and read control signals according to the reference clock, wherein each of the plurality of transmitter-receiver units respectively includes a delay generator circuit that sequentially accumulates a voltage level corresponding to the differential input signal based on the write control signals and sequentially outputs the accumulated voltage level based on the read control signals, wherein the delay generator circuit includes:
  a plurality of memory elements;
  a plurality of first switches that sequentially accumulate the voltage level of the differential input signal on the memory elements based on the write control signals,
  a plurality of second switches that sequentially output the voltage level accumulated on the memory elements based on the read control signals, and
  an operational amplifier that outputs a signal corresponding to the voltage level outputted from the second switches, wherein the digital circuit controls an output of the write control signals and the read control signals to vary a delay time between the accumulation of the voltage level of the differential input signal and the output of the voltage level accumulated on the memory elements, wherein, when a first delay time control signal that increases the delay time is inputted to the digital circuit, the digital circuit generates the read control signals that control the first switches to accumulate a same voltage level on two or more of the memory elements for a same period of the reference clock depending on an input period of the first delay time control signal, wherein, when a second delay time control signal that increases the delay time is inputted to the digital circuit, the digital circuit generates the read control signals that control the second switches to continue an output period of the voltage level outputted from one of the memory elements for a next period of the reference clock depending on an input period of the second delay time control signal, wherein, when a third delay time control signal that decreases the delay time is inputted to the digital circuit, the digital circuit generates the write control signals that control the first switches to continue an input period in which one of the memory elements accumulates the voltage level for a next period of the reference clock depending on an input period of the third delay time control signal, and when a fourth delay time control signal that decreases delay time of the reflected wave is inputted to the digital circuit, the digital circuit generates the read control signals that control the second switches not to output the voltage level from one or more of the memory elements for a next period of the reference clock depending on an input period of the fourth delay time control signal.

3. The ultrasound probe according to claim 2, wherein the delay generator circuit further includes a plurality of reset switches that reset the memory elements.

4. The ultrasound probe according to claim 2, wherein each of the memory elements is configured by a respective capacitor.

5. An ultrasound apparatus comprising the ultrasound probe according to claim 2.

6. The ultrasound probe according to claim 1, wherein each of the memory elements is configured by a respective capacitor.

7. An ultrasound apparatus comprising the ultrasound probe according to claim 1.

* * * * *